(12) United States Patent
Kwon

(10) Patent No.: US 7,829,088 B2
(45) Date of Patent: Nov. 9, 2010

(54) COMPOSITION COMPRISING HUMANIZED ANTIBODY HBBK4 FOR THE TREATMENT OF CANCER AND THE USE THEREOF

(75) Inventor: Byoung Se Kwon, Ulsan (KR)

(73) Assignee: University of Ulsan Foundation for Industry Cooperation, Ulsan (KR)

( * ) Notice: Subject to any disclaimer, the term of this patent is extended or adjusted under 35 U.S.C. 154(b) by 116 days.

(21) Appl. No.: 11/915,371

(22) PCT Filed: May 24, 2006

(86) PCT No.: PCT/KR2006/001963

§ 371 (c)(1),
(2), (4) Date: Nov. 23, 2007

(87) PCT Pub. No.: WO2006/126835

PCT Pub. Date: Nov. 30, 2006

(65) Prior Publication Data

US 2009/0041763 A1 Feb. 12, 2009

(30) Foreign Application Priority Data

May 24, 2005 (KR) ...................... 10-2005-0043854

(51) Int. Cl.
*A61K 39/00* (2006.01)
*A61K 39/395* (2006.01)
*C07K 16/00* (2006.01)
*C12P 21/08* (2006.01)

(52) U.S. Cl. .............. 424/133.1; 424/130.1; 424/138.1; 530/387.1; 530/387.3; 530/387.7

(58) Field of Classification Search ........................ None
See application file for complete search history.

(56) References Cited

U.S. PATENT DOCUMENTS 7,585,960 B2 * 9/2009 Hanke et al. .............. 536/23.53
7,592,426 B2 * 9/2009 Ebel et al. ................. 530/387.3
7,658,925 B2 * 2/2010 Groen et al. ............. 424/164.1

OTHER PUBLICATIONS

Melero, Shuford, Newby, Aruffo, Ledbetter, Hellstrom, Mittler, and Chen. Monoclonal antibodies against the 4-1BB T-cell activation molecule eradicate established tumors. Nature Medicine, 1997. vol. 3, pp. 682-685.*
Kocak, Chang, May, Abdessalam, Exten, Martin, Shen, Zheng, and Liu. AACR Meeting Abstract, Proceedings of the American Association of Cancer Research, 2005. vol. 46 (Suppl. 6) p. 1008. Abstract #4268.*
Kocak, Lute, Chang, May, Exten, Zhang, Abdessalam, Lehman, Jarjoura, Zheng, and Liu. Combination therapy with anti-CTL antigen-4 and anti-4-1BB antibodies enhances cancer immunity and reduces autoimmunity. Cancer Research, 2006. vol. 66 (14) pp. 7276-7284.*
Nagorsen D. et al., Clin. Cancer Res. 9, pp. 4296-4303, 2003.
Yee C. et al., J. Exp. Med. 192, pp. 1637-1644, 2000.
Mondino A et al., J. Leukoc. Biol. 55, pp. 805-815, 1994.
Berzofsky, J.A. et al., J. Clin. Invest. 113, pp. 1515-1525, 2004.
Dunn CF et al., Immunity 21, pp. 137-148, 2004.
Ye Z et al., Nat. Med. 8, pp. 343-348, 2002.
Phan GQ et al., Proc. Natl. Acad. Sci. USA, 100, pp. 8372-8377, 2003.
Yu P et al., Nat. Immunol. 5, pp. 141-149, 2004.
Iwai Y et al., Int. Immunol. 17.pp. 133-144, 2005.
Arens R et al., J. Exp. Med. 199, pp. 1595-1605, 2004.
Shuford WW. et al, J. Exd. Med. 186, pp. 47-55, 1995.
Francia G et al., Cancer Res. 56, 3855-3858, 1996.
Seo SK et al., Nat. Med., 10, pp. 1088-1094, 2004.
Castelli C. et al., J. Cell Physiol., 182, pp. 323-331, 2000 (Abstract).
Li Q et al., J. Immunother., 25, pp. 304-313, 2002 (Abstract).

* cited by examiner

*Primary Examiner*—Anne M. Gussow
(74) *Attorney, Agent, or Firm*—Hogan Lovells US LLP

(57) ABSTRACT

The present invention is related to a pharmaceutical composition comprising humanized anti-4-1BB antibody (HBBK4) for treating cancer by inducing increase of CD11+CD8+ T cell and IFN-γ, and inhibiting proliferation of cancer cells, together with a pharmaceutically acceptable carrier and the use. Accordingly, it can be useful in the prevention or treatment of cancer without adverse response.

4 Claims, 23 Drawing Sheets

Figure 1

BBK-4-H

```
                        # # #    @# #                *
m4B4-H         QVQLQQPGAELVKPGASVKLSCKASGYTFSSYWMHWVKQRPGQVLEWIGEINPGNGHTNYNEKFKSKATL
Human VH1-46/J4 QVQLVQSGAEVKKPGASVKVSCKASGYTFTSYYMHWVRQAPGQGLEWMGIINPSGGSTSYAQKFQGRVTM
H4B4-H         QV*L**SGAEVKKPGASVK*SCKASGYTFSSYWMHW*Q*PGQGLEWIGEINPGNGHTNYNEKFKS**TM
H4B4-H-2       QVQLQQSGAEV*KPGASVK*SCKASGYTFSSYWMHWV*QAPGQGLEWIGEINPGNGHTNYNEKFKS**T*
                    # # #         #
m4B4-H         TVDKSSSTAYMQLSSLTSEDSAVYYCARSFTTARAFAYWGQGTLVTVSS
Human VH1-46/J4 TRDTSTSTVYMELSSLRSEDTAVYYCAR    YFDYWGQGTLVTVSS
H4B4-H         TRDTSTSTVYMELSSLRSED*AVYYCARSFTTARAFAYWGQGTLVTVSS
H4B4-H-2       T*DTSTST*YM*LSSLRSED*AVYYCARSFTTARAFAYWGQGTLVTVSS
```

BBK-4-L

```
                      @           * *  ###    # #
m4B4-L         DIVMTQSQATQSVTPGDRVSLSCRASQTISDYLHWYQQKSHESPRLLIKYASQSISGIPSRFSGSGSGSDFTLS
Human A14/J2   DVVMTQSPAFLSVTPGEKVTITCQASEGIGNYLYWYQQKPDQAPKLLIKYASQSISGVPSRFSGSGSGTDFTFT
H4B4-L         D**MTQSPA*LSVTPGEKVT**CRASQTISDYLHWYQQK*D**P*LLIKYASQSISG*PSRFSGSGSG*DFTFT
H4B4-L-2       D*VMTQSPAFLSVTPGEKVT*TCRASQTISDYLHWYQQKPDQ*PKLLIKYASQSISG*PSRFSGSGSGTDFT**
                    # *#  * # #    @
m4B4-L         IMSVEPEDVGVYYCQDGHSFPPTFGGGTKLEIK
Human A14/J2   ISSLEAEDAATYYCQQGNKHPWTFGQGTKLEIK
H4B4-L         ISSLEAEDAATYYCQDGHSFPPTFG*GTKLEIK
H4B4-L-2       ISS*EAED***YYCQDGHSFPPTFGQGTKLEIK
```

- Underlined: residues for antigen contact (m)
- *: canonical residues (m)
- #: residues at the domain of interface (m)
- @: unusual sequence (h)
- Solvent-exposed residues (h):
    H chain: 11-18, 68-85 (Kabat sequence)
    L chain: 15-20, 71-85 (Kabat sequence)

lane 1: HBBK4-75/pcDNA transfectant
lane 2: HBBK4-75/pcDNA18 transfectant
lane 3: 293 EBNA-negative control

Figure 7

Nucleotide sequence of HBBK4-75G1 gatctcaccATGGGATGGAGCTGTATCATCCTCTTCTTGGTAGCAACAGCTACAGGTGTCCACTCCCAGGTGCAGCTGCAGCAGT
CTGGGGCTGAAGTAATAAAGCCTGGGGCTTCAGTGAAGCTTTCCTGCAAGGCTTCTGGCTACACCTTCAGCAGCTACTGGATGCA
CTGGGTGAGGCAGGCACCTGGACAAGGCCTTGAGTGGATTGGAGAGATTAATCCTGGCAACGGTCATACTAACTACAATGAGAAG
TTCAAGAGCAGGGCAACTCTGACTGGGGACACCTCTACAAGCACAGTATACATGGAACTCAGCAGCCTGCGGTCTGAGGACACCG
CGGTCTATTACTGTGCAAGATCTTTTACTACGGCACGGGCGTTTGCTTACTGGGGCCAAGGGACCCTCGTGACCGTCTCCTCAGC
TTCCACCAAGGGCCCATCGGTCTTCCCCCTGGCACCCTCCTCCAAAAGCACCTCTGGGGGCACAGCGGCCCTGGGCTGCCTGGTC
AAGGACTACTTCCCCGAACCGGTGACGGTGTCGTGGAACTCAGGCGCCCTGACCAGCGGCGTGCACACCTTCCCGGCTGTCCTAC
AGTCCTCAGGACTCTACTCCCTCAGCAGCGTGGTGACCGTGCCCTCCAGCAGCTTGGGCACCCAGACCTACATCTGCAACGTGAA
TCACAAGCCCAGCAACACCAAGGTGGACAAAAAAAGTTTGAGTCCCAAATCTTGTGACAAAACTCATACTTGCCCGCCGTGCCCG
GCTCCGGAACTCCTGGGGGGACCGTCAGTCTTCCTCTTCCCCCCAAAACCCAAGGACACCCTCATGATCTCCCGGACCCCTGAGG
TCACATGCGTGGTGGTGGACGTGAGCCACGAAGACCCTGAGGTCAAGTTCAACTGGTACGTGGACGGCGTGGAGGTGCATAATGC
CAAGACAAAGCCGCGGGAGGAGCAGTACAACAGCACGTACCGTGTGGTCAGCGTCCTCACCGTCCTGCACCAGGACTGGCTGAAT
GGCAAGGAGTACAAGTGCAAGGTCTCCAACAAAGCCCTCCCAGCCCCCATCGAGAAAACCATCTCCAAAGCCAAAGGGCAGCCCC
GAGAACCACAGGTGTACACCCTGCCCCCATCCCGGGAGGAGATGACCAAGAACCAGGTCAGCCTGACCTGCCTGGTCAAAGGCTT
CTATCCCAGCGACATTGCCGTGGAGTGGGAGAGCAATGGGCAGCCGGAGAACAACTACAAGACCACGCCTCCCGTGCTGGACTCC
GACGGCTCCTTCTTCCTCTATAGCAAGCTCACCGTGGACAAGAGCAGGTGGCAGCAGGGGAACGTCTTCTCATGCTCCGTGATGC
ATGAGGCTCTGCACAACCACTACACGCAGAAGAGCCTCTCCCTGTCCCCGGGTAAATGA

Figure 8

Amino acid sequence of HBBK4-75G1

DLTMGWSCIILFLVATATGVHSQVQLQQSGAEVIKPGASVKLSCKASGYTFSSYWMHWVRQAPGQGLEWIGEINPGNGHTNYNEK
FKSRATLTGDTSTSTVYMELSSLRSEDTAVYYCARSFTTARAFAYWGQGTLVTVSSASTKGPSVFPLAPSSKSTSGGTAALGCLV
KDYFPEPVTVSWNSGALTSGVHTFPAVLQSSGLYSLSSVVTVPSSSLGTQTYICNVNHKPSNTKVDKKSLSPKSCDKTHTCPPCP
APELLGGPSVFLFPPKPKDTLMISRTPEVTCVVVDVSHEDPEVKFNWYVDGVEVHNAKTKPREEQYNSTYRVVSVLTVLHQDWLN
GKEYKCKVSNKALPAPIEKTISKAKGQPREPQVYTLPPSREEMTKNQVSLTCLVKGFYPSDIAVEWESNGQPENNYKTTPPVLDS
DGSFFLYSKLTVDKSRWQQGNVFSCSVMHEALHNHYTQKSLSLSPGK

Figure 9

Nucleotide sequence of HBBK4-75G4 gatctcaccATGGATGGAGCTGTATCATCCCTCTTCTTGGTAGCAACAGTACAGGTGTCCACTCCCAGGTGCAGCTGCAGCAGT
CTGGGGCTGAAGTAATAAAGCCTGGGGCTTCAGTGAAGCTTCCTGCAAGGCTTCTGGCTACACCTTCAGCAGTACTGGATGCA
CTGGGTGAGGCAGGCAGGCCACCTGGACAAGGCCTTGAGTGGATTGGAGAGATTAATCCTGGCAACGGTCATACTAACTACAATGAGAAG
TTCAAGAGCAGGGCAACTCTGACTGGGACACCTCTACAAGCACAGTATACATGGAACTCAGCAGCCTGCGGTCTGAGGACACCG
CGGTCTATTACTGTGCAAGATCTTTTACTGGCACGGGCGTTTGCTTACTGGGGCCAAGGGACCCTCGTGACCGTCTCCTCAgc ttccaccaaggccatccgtcttcccctggcgcctgctccaggagcacctcgagagcacagccgccctgggctgcctggtc
aaggactacttcccgaaccggtgacggtgtcgtggaactcaggcgcccctgaccagcagcggcgtgcacaccttccggctgtcctac
agtcctcaggactctactccctcagcagcgtggtgaccgtgcctccagcagcttgggcacgaagacctacacctgcaacgtaga
tcacaagcccagcaacaccaaggtggacaagagagttgagtccaaatatggtccccatcatgatctcccgaccctgagtcacgtgcttc
ctggggggaccatcagtcttcctgttcccccaaaaccaaggacactctcatgatctcccgaccctgaggtcacgtgcgtgg
tggtggacgtgagccaggaagacccgaggtccagttcaactggtacgtggatggcgtggaggtgcataatgccaagacaaagcc
gcgggaggagcagttcaacagcacgtaccgtcctgcaccgtcctgcaccaggactgctgaacggcaaggagtac
aagtgcaaggtctccaacaaagcctccgtcctccatcgagaaaccatctccaaagccaaagggcagccccgagagccacagg
tgtacaccctgccccccatcccaggaggagatgaccaagaaccagttcagcctgacctgcctggtcaaaggcttctacccagcga
catcgccgtggagtgggagagcaatgggcagccggagaacaactacaagaccacgcctcccgtgctggactccgacggctcctc
ttcctctacagcaggctaaccgtggacaagagcaggtggcaggaggggaatgtcttctcatgctccgtgatgcatgaggctctgc
acaaccactacacagaagagcctctccctgtctctgggtaaatga

Figure 10

Amino acid sequence of HBBK4-75G4

MGWSCIILFLVATATGVHSQVQLQQSGAEVIKPGASVKLSCKASGYTFSSYWMHWVRQAPGQGLEWIGEINPGNGHTNYNEKFKS
RATLTGDTSTSTVYMELSSLRSEDTAVYYCARSFTTARAFAYWGQGTLVTVSSASTKGPSVFPLAPCSRSTSESTAALGCLVKDY
FPEPVTVSWNSGALTSGVHTFPAVLQSSGLYSLSSVVTVPSSSLGTKTYTCNVDHKPSNTKVDKRVESKYGPPCPSCPAPEFLGG
PSVFLFPPKPKDTLMISRTPEVTCVVVDVSQEDPEVQFNWYVDGVEVHNAKTKPREEQFNSTYRVVSVLTVLHQDWLNGKEYKCK
VSNKGLPSSIEKTISKAKGQPREPQVYTLPPSQEEMTKNQVSLTCLVKGFYPSDIAVEWESNGQPENNYKTTPPVLDSDGSFFLY
SRLTVDKSRWQEGNVFSCSVMHEALHNHYTQKSLSLSLGK

Figure 11

Nucleotide sequence of HBBK4-75L gcctggacatgATGAGGTTCTCTGCTCAGTTCCTTGGTCTCCTGTTGCTCCTCGTTTTCAAGGTACCAGATGTGACATTGTGATGAC
TCAGTCTCCAGCCTTCTTATCTGTGACTCCAGGAGAAAGTGACTATTACTGCAGGGCCAGCCAGACTATTAGGGACTACTTA
CACTGGTATCAACAAAAACCCGATCAAGCTCCCAAACTTCTCATCAAATATGCTTCCCAATCCATCTCTGGGATTCCCTCCAGGT
TCAGTGGCAGTGGATCAGGGACTGATTTCACTTTTACTATCTCGTCGCTCGAGGCAGAAGATGCTGGGAGCTATTACTGTCAAGA
TGGTCACAGCTTTCCCCAACTTTCGGTCAAGGAACTAAACTCGAGATCAAAactgtggctgcaccatctgtcttcatcttcccg
ccatctgatgagcagttgaaatctggaactgcctctgttgtgtgcctgctgaataacttctatcccagagaggccaaagtacagt
ggaaggtggataacgccctccaatcgggtaactcccaggagagtgtcacagagcaggacagcaaggacagcacctacagcctcag
cagcaccctgacgctgagcaaagcagactacgagaaacacaaagtctacgcctgcgaagtcacccatcagggcctgagttcgccc
gtcacaaagagcttcaacaggggagagtgttag

Figure 12

Amino acid sequence of HBBK4-75L

LDMRFSAQFLGLLLLCFQGTRCDIVMTQSPAFLSVTPGEKVTITCRASQTISDYLHWYQQKPDQAPKLLIKYASQSISGIPSRF
SGSGSGTDFTFTISSLEAEDAATYYCQDGHSFPPTFGQGTKLEIKTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

COMPOSITION COMPRISING HUMANIZED ANTIBODY HBBK4 FOR THE TREATMENT OF CANCER AND THE USE THEREOF

This application is the U.S. National Phase under 35 U.S.C. §371 of International Application PCT Patent Application No. PCT/KR2006/001963, filed on May 24, 2006, which claims priority to Korean Patent Application No. 10-2005-43854, filed on May 24, 2005, the contents of which are all herein incorporated by this reference in their entireties. All publications, patents, patent applications, databases and other references cited in this application, all related applications referenced herein, and all references cited therein, are incorporated by reference in their entirety as if restated here in full and as if each individual publication, patent, patent application, database or other reference were specifically and individually indicated to be incorporated by reference.

TECHNICAL FIELD

The present invention relates to a pharmaceutical composition comprising humanized antibody HBBK4 for treating or preventing cancer disease and the use thereof.

BACKGROUND ART

Cancer cells express cancer cell-specific antigen resulting from the inductions of over-expression and mutation for specific proteins, which are removed due to the auto immune reaction of patient (Nagorsen D. et al., *Clin. Cancer Res.* 9, pp 4296-4303, 2003; Yee C et al., *J. Exp. Med.* 192, pp 1637-1644, 2000; Castelli C et al., *J. Cell Physiol.*, 182, pp 323-331, 2000). Those immune reactions against cancer cells are represented by antigen-presenting cell (APC) such as dendritic cell which is the same with normal immune reaction and the cancer cells are removed by activation of appropriate T cell and B cell with APC (Jay A. et al., *J. Clin. Invest.* 113, pp 1515-1525, 2004).

Cancer cells cause anergy or tolerance through various mechanisms for examples, the decrease of MHC molecules, inhibition of co-stimulatory molecule expression, induction of immunosuppressive substance such as TGF-β and IL-10, infiltration of CD4+CD25+ regulatory T cell in cancer tissues etc, and try to protecting from the anti-cancer immune reaction (Smyth M J et al., *Nat. Immunol.* 2, pp 293-299, 2001; Dunn G P et al., *Immunity* 21, pp 137-148, 2004). The anti-cancer immune reactions depend on cell-mediated immunity. In particular, CD8+ T cells (CTLs) are critical to remove cancers, and keep the immunologic memory (Maeurer M J et al., *Int. Rev. Immunol.* 14, pp 97-132, 1997).

There need two kinds of signals to induce T cell activation (Mondino A et al., *J. Leukoc. Biol.* 55, pp 805-815, 1994), i.e., first signal, namely antigen specific signal, is carried out by TCR and the second signal is carried out by co-stimulatory molecules. Ig (immunoglobulin) family and TNFR family are well known as co-stimulatory molecules. Since the immune agonistic and antagonistic roles of those molecules were publicly known, various treatment methods using thereby have been tried till now. At present, there have been reported that 4-1BB (CD137), CTLA-4, CD28, LIGHT, PD-1, CD27 etc showed potent anti-cancer activity among them (Ye Z et al., *Nat. Med.* 8, pp 343-348, 2002; Phan G Q et al., *Proc. Natl. Acad. Sci. USA*, 100, pp 8372-8377, 2003; Li Q et al., *J. Immunother.*, 25, pp 304-313, 2002; Yu P et al., *Nat. Immunol.* 5, pp 141-149, 2004; Iwai Y et al., *Int. Immunol.* 17, pp 133-144, 2005; Arens R et al., *J. Exp. Med.* 199, pp 1595-1605, 2004).

There have been reported that 4-1BB induces the expression of CTL and IFN-γ, and agonistic anti-4-1BB mAb on cancer treatment have been tried by many researchers (Shuford W W. et al, *J. Exp. Med.* 186, pp 47-55, 1997).

CTLA-4 has been reported to limit the immune reaction and the inhibition of CTLA-4 signal transfer expressed by activated T cells prevents the proliferation of cancer cell due to maximized activation of T cell (Phan G Q et al., *Proc. Natl. Acad. Sci. USA*. 100, pp 8372-8377, 2003).

The present inventors have been tried to discover the function of anti-4-1BB antibody and finally found that the treatment using by agonistic anti-4-1BB antibody and antagonistic anti-CTLA-4 antibody increases cancer cell-specific CD8+ T cell, which induces the production of CD8+ T cell expressing CD11c molecule resulting in infiltrating into the tumor differently from other co-stimulatory molecules. The inhibition of cancer cell proliferation through the administration of agonistic anti-4-1BB antibody is caused by the abundant infiltration of CD11c+CD8+ T cells in tumor and highly expressed IFN-γ.

Accordingly, the present invention has been completed by confirming that the treating effect of humanized anti-4-1BB antibody and/or antagonistic anti-CTLA-4 antibody on cancer is caused by increased CD11c+CD8+ T cell resulting in potent inhibiting effect on cancer by the intensification of CTL function and IFN-γ expression and further the effect is reinforced by the inhibition of CTLA-4 signal transfer.

These and other objects of the present invention will become apparent from the detailed disclosure of the present invention provided hereinafter.

DISCLOSURE

Technical Problem

According to one aspect of present invention, the present invention provides a pharmaceutical composition comprising humanized anti-4-1BB antibody (HBBK4) for treating or preventing cancer disease through the induction of CD11+CD8+ T cell and IFN-γ expression increase as an effective ingredient, together with a pharmaceutically acceptable carrier.

The present invention provides an immunotherapeutic method for treating or preventing cancer disease comprising administering to mammal an effective amount of humanized anti-4-1BB antibody (HBBK4) as an effective ingredient, together with a pharmaceutically acceptable carrier thereof.

The present invention also provides a use of humanized anti-4-1BB antibody (HBBK4) for the preparation of therapeutic agent for treating or preventing cancer disease in a mammal including human in need thereof.

Technical Solution

Accordingly, it is an object of the present invention to provide a pharmaceutical composition comprising humanized anti-4-1BB antibody (hereinafter designated as HBBK4) for treating or preventing cancer disease through the induction of CD11+CD8+ T cell increase as an effective ingredient, together with a pharmaceutically acceptable carrier.

In accordance with another aspect of the present invention, there is also provided a use of humanized anti-4-1BB antibody (HBBK4) for the preparation of therapeutic agent for treating and preventing cancer disease in a mammal including human in need thereof.

In accordance with the other aspect of the present invention, there is also provided immunotherapeutic method for treating or preventing cancer disease comprising administering to mammal in an effective amount of humanized anti-4-1BB antibody (HBBK4) as an effective ingredient, together with a pharmaceutically acceptable carrier thereof.

In accordance with the other aspect of the present invention, there is also provided a pharmaceutical composition comprising the combined of humanized anti-4-1BB antibody and anti-CTLA-4 antibody for treating or preventing cancer disease through the synergic inhibition effect on cancer cell proliferation as an effective ingredient, together with a pharmaceutically acceptable carrier.

In accordance with another aspect of the present invention, there is also provided a use of the combined mixture humanized anti-4-1BB antibody and anti-CTLA-4 antibody for the preparation of therapeutic agent for treating and preventing cancer disease in a mammal including human in need thereof.

In accordance with the other aspect of the present invention, there is also provided immunotherapeutic method for treating or preventing cancer disease comprising administering to mammal in an effective amount of the combined mixture humanized anti-4-1BB antibody and anti-CTLA-4 antibody as an effective ingredient, together with a pharmaceutically acceptable carrier thereof.

The pharmaceutical composition for treating or preventing cancer disease of the present invention could contain about 0.01 to 80 w/w %, preferably 0.1 to 50 w/w % of the above-described humanized anti-4-1BB antibody (HBBK4) of the present invention based on the total weight of the composition The term "humanized anti-4-1BB antibody (HBBK4)" disclosed herein can comprises nucleotide sequence of Seq. ID: 59, Seq. ID: 61 or Seq. ID: 63 and also comprises amino acid sequence of Seq. ID: 60, Seq. ID: 62 or Seq. ID: 64.

The term "cancer disease" disclosed herein comprise lung cancer, arsenic cellular lung cancer, colon cancer, bone cancer, pancreatic cancer, skin cancer, cephalic or cervical cancer, skin or endophthalmic melanoma, hysterocarcinoma, ovarian cancer, rectal cancer, stomach cancer, perianal cancer, colonic cancer, breast cancer, endometrioma, cervical carcinoma, vaginal carcinoma, vulvul carcinoma, Hodgkin's disease, esophageal cancer, enteric cancer, endocrine gland cancer, thyroid cancer, parathyroid cancer, adrenal cancer, smooth tissue sarcoma, urethral cancer, penile cancer, prostatic cancer, chronic or acute leukemia, lymphocytoma, cystic cancer, nephritic or hydroureteric cancer, renal cell carcinoma, renal pelvic carcinoma, CNS tumor, primary CNS lymphoma, spinal medulla tumor, brain stem neuroglioma, hypophyseal adenomatosis and the like.

Hereinafter, the present invention is described in detail.

For the present invention, the humanized anti-4-1BB antibody (HBBK4) disclosed herein can be prepared by following procedure;

For example, HBBK4 of the present invention can be prepared by the procedure comprising the steps; preparing agonistic anti-4-1BB antibody (BBK4) using by hybridoma cell line at $1^{st}$ step; cloning of BBK4 gene at $2^{nd}$ step; humanizing VH and VL of BBK4 at $3^{rd}$ step; selecting humanized BBK4 (HBBK4) clone through the function analysis of humanized BBK4 (HBBK4) ScFv at last step to obtain HBBK4 of the present invention.

Therefore, the inventive HBBK4 prepared by methods described above, can be used as an active ingredient in preparing a pharmaceutical composition to prevent and treat cancer disease.

Furthermore, combined mixture of HBBK4 prepared by methods described above and anti-CTLA-4 antibody, can be used as an active ingredient in preparing a pharmaceutical composition to prevent and treat cancer disease.

The inventive composition may additionally comprise appropriate carriers, adjuvants or diluents, conventionally used in the art. The appropriate carriers, adjuvants or diluents is not limited to a specific material, and can be chosen, according to the usage and application method. Appropriate diluents are listed in the written text of Remington's Pharmaceutical Science (Mack Publishing Co., Easton Pa.).

The inventive HBBK4 antibody can be used independently or in combination with well-known cancer drugs such as taxol, cyclophosphamide, doxorubicin and the like.

Hereinafter, the following formulation methods and excipients are merely exemplary and in no way limit the invention.

The composition according to the present invention can be provided as a pharmaceutical composition containing pharmaceutically acceptable carriers, adjuvants or diluents, e.g., lactose, dextrose, sucrose, sorbitol, mannitol, xylitol, erythritol, maltitol, starches, acacia rubber, alginate, gelatin, calcium phosphate, calcium silicate, cellulose, methyl cellulose, polyvinyl pyrrolidone, water, methylhydroxy benzoate, propylhydroxy benzoate, talc, magnesium stearate and mineral oil. The formulations may additionally include fillers, anti-agglutinating agents, lubricating agents, wetting agents, flavoring agents, emulsifiers, preservatives and the like. The compositions of the invention may be formulated so as to provide quick, sustained or delayed release of the active ingredient after their administration to a patient by employing any of the procedures well known in the art.

For example, the composition of the present invention can be dissolved in oils, propylene glycol or other solvents which are commonly used to produce an injection. Suitable examples of the carriers include physiological saline, polyethylene glycol, ethanol, vegetable oils, isopropyl myristate, etc., but are not limited to them. For topical administration, the compounds of the present invention can be formulated in the form of ointments and creams.

Pharmaceutical formulations containing inventive composition may be prepared in any form, such as oral dosage form (powder, tablet, capsule, soft capsule, aqueous medicine, syrup, elixirs pill, powder, sachet, granule), or topical preparation (cream, ointment, lotion, gel, balm, patch, paste, spray solution, aerosol and the like), or injectable preparation (solution, suspension, emulsion).

The composition of the present invention in pharmaceutical dosage forms may be used in the form of their pharmaceutically acceptable salts, and also may be used alone or in appropriate association, as well as in combination with other pharmaceutically active compounds.

The desirable dose of the inventive composition varies depending on the condition and the weight of the subject, severity, drug form, route and period of administration, and may be chosen by those skilled in the art. However, in order to obtain desirable effects, it is generally recommended to administer at the amount ranging 10 mg/kg, preferably, 0.1 to 1000 mg/kg by weight/day of the inventive extract or composition of the present invention. The dose may be administered in single or divided into several times per day.

In terms of composition, the inventive composition should be present between 0.01 to 80% by weight, preferably 0.5 to 50% by weight based on the total weight of the composition.

The pharmaceutical composition of present invention can be administered to a subject animal such as mammals (rat, mouse, domestic animals or human) via various routes. All modes of administration are contemplated, for example, administration can be made orally, rectally or by intravenous, intramuscular, subcutaneous, intracutaneous, intrathecal, epidural or intracerebroventricular injection.

It will be apparent to those skilled in the art that various modifications and variations can be made in the compositions, use and preparations of the present invention without departing from the spirit or scope of the invention.

The present invention is more specifically explained by the following figures and examples. However, it should be understood that the present invention is not limited to these examples in any manner.

ADVANTAGEOUS EFFECTS

The inventive HBBK4 antibody of the present invention showed inhibition effect on cancer cell proliferation caused by increase of CD11c+CD8+ T cell population and IFN-γ expression. Accordingly, it can be useful in the prevention or treatment of cancer diseases without adverse response.

DESCRIPTION OF DRAWINGS

The above and other objects, features and other advantages of the present invention will more clearly understood from the following detailed description taken in conjunction with the accompanying drawings, in which;

FIG. 1 presents a humanizing design of agonistic anti-4-1BB antibody [amino acid sequence of BBK-4-H m4B4-H—SEQ. ID: 65; amino acid sequence of BBK-4-H Human VH1-46/J4—SEQ. ID: 66; amino acid sequence of BBK-4-H M4B4-H—SEQ. ID: 67; amino acid sequence of BBK-4-H H$_4$B4-H-2—SEQ. ID: 68; amino acid sequence of BBK-4-H m4B4-H—SEQ. ID: 69; amino acid sequence of BBK-4-H Human VH1-46/J4—SEQ. ID: 70; amino acid sequence of BBK-4-H M4B4-H—SEQ. ID: 71; amino acid sequence of BBK-4-H H$_4$B4-H-2-SEQ. ID: 72; amino acid sequence of BBK-4-L m4B4-L—SEQ. ID: 73; amino acid sequence of BBK-4-L Human A14/J2—SEQ. ID: 74; amino acid sequence of BBK-4-L H$_4$B4-L—SEQ. ID: 75; amino acid sequence of BBK-4-L H$_4$B4-L-2—SEQ. ID: 76; amino acid sequence of BBK-4-L m4B4-L—SEQ. ID: 77; amino acid sequence of BBK-4-L Human A14/J2—SEQ. ID: 78; amino acid sequence of BBK-4-L H$_4$B4-L—SEQ. ID: 79; amino acid sequence of BBK-4-L H$_4$B4-L-2—SEQ. ID: 80]

FIG. 7 shows a nucleotide sequence of HBBK4-75G1 [SEQ. ID: 59].

FIG. 8 shows an amino acid sequence of HBBK4-75G1 [SEQ. ID: 60].

FIG. 9 shows a nucleotide sequence of HBBK4-75G4 [SEQ. ID: 61].

FIG. 10 represents an amino acid sequence of HBBK4-75G4 [SEQ. ID: 62].

FIG. 11 represents a nucleotide sequence of HBBK4-75L [SEQ. ID: 63].

FIG. 12 represents an amino acid sequence of HBBK4-75L [SEQ. ID: 64].

BEST MODE

Figure 2:
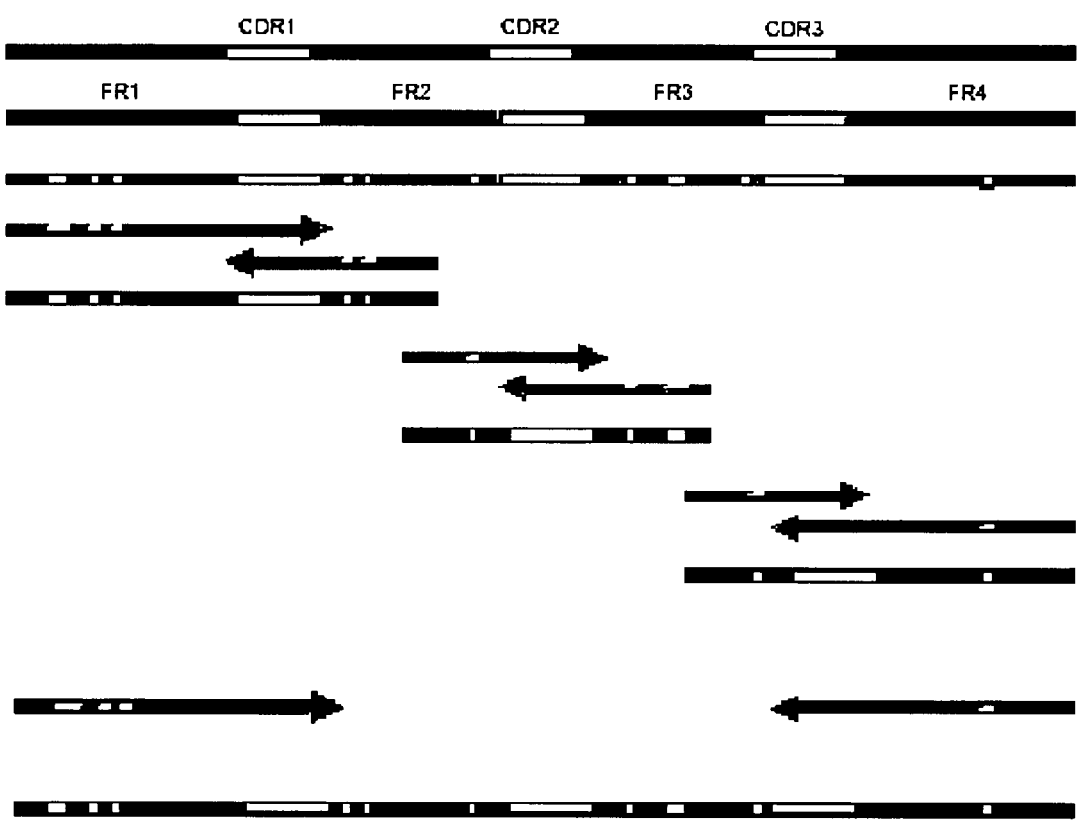
FIG. 2 presents a primer design for producing humanized ScFv of BBK4.

It will be apparent to those skilled in the art that various modifications and variations can be made in the composition, use and preparations of the present invention without departing from the spirit or scope of the invention.

The present invention is more specifically explained by the following examples. However, it should be understood that the present invention is not limited to these examples in any manner.

EXAMPLES

The following Example and Experimental Examples are intended to further illustrated the invention without limiting its scope.

Example 1

Preparation of Agonistic Anti-Human 4-1BB (BBK4)

1-1. Preparation of human 4-1BB protein pGEX3 expression vector was prepared by combining cDNA coding human 4-1BB molecule with DNA (Pharmacia LKB Biotechnology) coding the binding site of glutathion-S-transferase (GST).

After transforming *E. Coli* with the above vector, it was cultured under the proper condition to induce the expression of 4-1BB-GST fusion protein, and then 4-1BB-GST fusion protein was obtained by performing further separation and purification using by glutathion sepharose-4B column (Pharmacia LKB Biotechnology).

1-2. Immunity

20 μg of 4-1BB-GST and 0.1 ml of Freund complete adjuvant was mixed and administrated into the abdominal cavity of Balb/c mice aged from 4 to 8 weeks to induce minimal immune response. The mixture of 20 μg of 4-1BB-GST and Freund incomplete adjuvant was administered into the abdominal cavity of Balb/c mice twice at the interval of three weeks to induce immunity.

Three days after the end of immunity, the titer of antibody was determined according to enzyme immuno assay (EIA) by collecting small quantity of blood sample from tail, and the spleen cell obtained by delivered spleen was used to cell fusion when the immune value reached at specific level.

1-3. Cell Fusion

The spleen cell obtained from immunized mouse was mixed with SP2/0-Ag14 myeloma cell (ATCC CRL 1581) with the mixed ratio of 1:2, and fused by using polyethylene glycol 4000 (Gibco). Following experiment was performed by the procedure disclosed in the literature (Mishell and Shiigi, *Selected Methods in Cellular immunology*. W. H. Freeman Company, 1980)

To select hybridoma cells, the fused cell mixture was suspended in HAT medium, i.e., supplemented RPMI medium with 15% Fetal Calf Serum, 0.1 mM hypoxanthine, 0.4 μM aminopteridin and 16 μM thymidine, poured into 96 well micro culture tray in a concentration of $3 \times 10^7$ cells/ml and incubated with cell culture supplied with 5% $CO_2$ gas at 37° C. Since both of the myeloma cell and other non-fused spleen cell could not grow in HAT medium, only already fused cells had been regard as being grown in HAT medium. After each 6, 7 and 8 days, half of the culture medium was replaced with new culture medium. The antibody containing supernatant solution was collected from 96 well micro-culture plate when the cells were sufficiently grown with being examined by reverse phase microscope to perform ELISA method.

1-4. Selection Of Hybridoma Cell Line

The concentration of 4-1BB-GST was adjusted to 200 ng/0.1 ml by diluting with carbonate buffer solution (pH 9.6) and it was coated on ELISA plate. The completely coated plates were washed with phosphate buffered saline (PBS) solution and PBS containing 1% FBS albumin was thereto to let alone for 1 hour. The plates were washed with PBS several times and incubated with supernatant solution prepared in example 1-3 for 1 hr. After the incubation, the plates were washed with PBS several times and 0.1 ml of diluted alkaline phosphatase binding goat anti-mouse immunoglobulin (×1000, Southern Biotech) was added thereto. After one hour, the plates was washed with PBS several times and 0.1 ml of substrate solution prepared by dissolving p-nitrophenyl sodium monophosphate in carbonate buffer solution into 1 mg/ml (pH 9.6) was added thereto to store at room temperature for 10 mins. Through determining the reaction using by auto-micro plate recorder, the hybridoma cell line producing 4-1BB specific-binding antibody, which is designated as BBK-4 hereinafter.

1-5. Preparation of Antibody Using by Hybridoma Cell Line

The BBK-4 cell line ($1 \times 10^7$) prepared in example 1-4 was proliferated in the medium and intraperitoneally administrated into Balb/c mice pretreated with 0.5 ml of pristane (2,6,10,14-tetramethylpentadecane, Sigma) to collect ascites fluid. The fluid was subjected to affinity column chromatography using by protein-G sepharose column (Pharmacia) to isolate monoclonal antibody of the present invention of which producing rate of antibody is 1 mg/ml ascites fluid.

At the result of determination using by antibody analysis kit, the antibody of the present invention is determined to IgG1 having isotype of kappa light chain.

Example 2

Gene Cloning of Agonistic Anti-Human 4-1BB (BBK4)

2-1. mRNA of BBK-4 Clone

Total RNA was extracted from $2 \times 10^8$ cells of BBK-4 clone. The cell pellet was treated with TriPure Isolation Reagent (Sigma) and subjected to extraction with Phenol/chloroform one time. The supernatant was treated with isopropanol to precipitate RNA. The RNA was washed with 75% ethanol twice, dissolved in DEPC'd water to obtain total RNA. The extraction of mRNA was performed by Dynalbeads mRNA purification kit (DYNAL).

2-2. cDNA Library Preparation of BBK-4 Clone

ZAP-cDNA synthesis kit and ZAP-cDNA Gigapack III Gold Cloning (STRATAGENE) were used to prepare cDNA library of BBK-4.

2-2-1. First Strand Synthesis

The extracted mRNA prepared in example 2-1 was used to synthesis first strand of BBK4. The mixture of 5 μg of mRNA, linker primer, RNase H-reverse transcriptase, methyl nucleotide mixture and RNase inhibitor was reacted at 37° C. for one hour. Linker primer has Xho I site and sequence of SEQ. ID: 1.

2-2-2. Second Strand Synthesis

The RNase H and DNA polymerase I was used to synthesis second strand and the mixture was reacted at 16° C. for 2.5 hours. After the reaction, the reactant was subjected to phenol/chloroform extraction and concentrated using by ethanol. The concentrates were washed with 70% ethanol, dissolved in water and the protein was removed by Utrafree-Probind filter (Sigma).

2-2-3. Blunting the cDNA Termini

Both 3'-end and 5'-end of cDNA were blunted with Klenow fragment and dNTP. The protein was removed by Utrafree-Probind filter (Sigma).

2-2-4. Ligation EcoRI Adaptors

Both of rATP and T4 DNA ligase were added thereto. The solution was reacted at 4° C. for 12 hours and heated to inactivate the enzyme at 70° C. for 30 minutes.

2-2-5. Kinasing the EcoRI Ends

Both of rATP and T4 polynucleotide kinase were added thereto. The solution was reacted at 37° C. for 30 minutes and heated to inactivate the enzyme at 70° C. for 30 minutes.

2-2-6. Xho I Digestion

Digestion was performed using by Xho I and the protein was removed by Utrafree-Probind filter (Sigma).

2-2-7. Ligating cDNA into Uni-ZAP XR Vector Arms

The amount of prepared cDNA was determined by using Ethidium bromide. The mixture of 100 ng cDNA and 125 μg Uni-ZAP XR vector was reacted at 12° C. for 12 hours using by rATP and T4 DNA ligase.

2-2-8. Packaging

At the beginning of melting packaging extract which was stored at −80° C., 2 μg of ligated DNA was added thereto carefully in order not to form bubble and mixed with pippet. The solution was reacted for 2 hours and mixed with 500 μg of SM buffer solution containing 100 mM NaCl, 10 mM $MgSO_4 \cdot 7H_2O$, 50 mM Tris-HCl (pH 7.5) and 0.01% gelatin and 20 μl of chloroform. The solution was centrifuged and the supernatant was transferred to new tube.

2-2-9. Titering the Library

XL-1 Blue MRF' was used as a host cell and the single colony prepared by inoculating on LB/tetracycline plate (60 µg/ml) was inoculated into LB medium containing 10 mM MgSO$_4$ and 0.2% maltose. The colony was cultured with vibrating at the speed 200 rpm in order not to exceed 1.0 of OD$_{600}$ at 37° C. The culture was centrifuged for 10 mins at the speed of 500×g to remove the medium and 10 mM MgSO$_4$.7H$_2$O was added to the cell pellet to the extent the OD$_{600}$ reaches to 0.5. The prepared host cell was stored at 4° C. to let the cell alive for 48 hours. 1 µl of diluted packaged reaction to 1/10 was added to 200 µl of host cell and attached to the host cell at 37° C. for 15 minutes. 3 ml of cooled top agar at 48° C. was added thereto, subjected to vortexing and poured to preheated LB agar plate. The cells were grown at 37° C. for 10 hours and the cell number was calculated by counting the number of plaques (pfu/ml). It has been confirmed that final counted cell number was 1.9×10$^6$ pfu.

2-3. Screening of Heavy Chain Gene and Kappa Chain Gene

The above cells were subjected to plate in order to form about 200-300 plaques per 100 mm and transferred to nylon membrane to make UV cross linking. Hybridization was performed using by the membrane. Each completed fragment cloned by PCR was used as a probe for screening heavy chain and kappa chain. ECL direct nucleic acid labeling and detection kit was used to hybridization. The clones were transformed into plasmids through in vivo removal system using the Exassit/SOLR and the sequence was determined by sequencing method.

Example 3

VH and VL Humanization of Agonistic Anti-Human 4-1BB (BBK4)

3-1. Selection of Human Homolog VH and VL of BBK-4 Clone

The similar one among human antibody genes to the V region sequence of clone BBK-4 coding mouse protein was selected through data base search system. The sequence comparing with BBK-4 sequence was used for preparing PCR template and primer necessary to prepare combinatorial antibody library.

3-2. Design for Humanization of BBK-4 Gene

The CDR and FR part region in heavy and light chain of BBK-4 was determined and the standard to determine whether the region was changed to human amino acid residue or remained not was followed pursuant to the rule disclosed in Table 1.

CDR region, i.e., the directly linked region with antigen among lots of part sequences of H and L chain was used in mouse sequence and canonical region was used in mouse sequence. The sequence positioned at interface between H and L chain was used in mouse sequence although it existed at FR region and specific sequence was used in human sequence. The solvent exposed residue was used in mouse sequence and the humanized nucleotide sequence was determined based on the protocol (See FIG. 1).

TABLE 1

| Mouse residue | Comments | Decision |
| --- | --- | --- |
| CDR | According to Ig Blast (www.ncbi.nlm.nih.gov) | Mouse |
| Canonical residues | Chothia canonical assignment (www.cryst.bbk.ac.uk/~ubcg07s/) | Mouse |
| Interchain packing residues | | Mouse |
| N-glycosylation sites | | Human |
| Unusual framework residues | Any residues within 5-6 A° of any CDR residues | Mouse |
| | All the other residues | Human |
| Solvent-exposed residues | Any residues of CDR, canonical, interchain | Mouse |
| | All the other residues (imgt.cines.fr:8104/textes/IMGTrepertoire.html) | Human |

3-3. Primer Preparation to Make Combinatorial Antibody Library.

To prepare insertion for preparing combinatorial antibody library, the combinatorial primer was prepared based on amino acid sequence obtained by comparing the heavy and light chain sequences of BBK-4 clone with human template. The primer sequences were shown as SEQ. ID: 2-SEQ. ID: 18 and in Table 2.

TABLE 2

```
primer    Sequence

HBBK4-1U  5'-actgcggcccagccggccatggcccaggtgcagctgcag
SEQ.        cagtctggggctgaagtarwaaagcctggggc -3'
ID: 2

HBBK4-1D  5'-agtagctgctgaaggtgtagccagaagccttgcaggaaa
SEQ.        scttcactgaagcccaggctttwytacttc -3'
ID: 3

HBBK4-2U  5'-tacaccttcagcagctactggatgcactgggtgargcag
SEQ.        gcacctggacaaggccttgagtggattggag -3'
ID: 4

HBBK4-2D  5'-tgctcttgaacttctcattgtagttagtatgaccgttgc
SEQ.        caggattaatctctccaatccactcaaggcc -3'
ID: 5

HBBK4-3U  5'-aatgagaagttcaagagcarggyaactmtgactskggac
SEQ.        acctctacaagcacagyatacatgsaactca -3'
ID: 6

HBBK4-3D  5'-taaaagatcttgcacagtaatagaccgcggwgtcctcag
SEQ.        accgcaggctgctgagttscatgtatrctgt -3'
ID: 7

HBBK4-4U  5'-tactgtgcaagatcttttactacggcacgggcgtttgct
SEQ.        tactggggccaagggaccctcgtgaccgtct -3'
ID: 8

HBBK4-4D  5'-ctgagccgccgccgcctgagccgccgccgcctgagccgc
SEQ.        cgccgcctgaggagacggtcacgagggtccc -3'
ID: 9

HBBK4-5U  5'-tcaggcggcggcggctcagacrttgtgatgactcagtct
SEQ.        ccagccttcttatctgtgactccaggagaga -3'
ID: 10

HBBK4-5D  5'-agtgtaagtagtcgctaatagtctggctggccctgcaag
SEQ.        taakagtcactttctctcctggagtcacaga -3'
ID: 11

HBBK4-6U  5'-attagcgactacttacactggtatcaacaaaaacccgat
SEQ.        caakctcccaaacttctcatcaaatatgctt -3'
ID: 12
```

TABLE 2-continued

| primer | Sequence |
|---|---|
| HBBK4-6D SEQ. ID: 13 | 5'-tccctgatccactgccactgaacctggagggaaycccag agatggattgggaagcatatttgatgagaag -3' |
| HBBK4-7U SEQ. ID: 14 | 5'-agtggcagtggatcagggactgatttcactyttastatc tcgtcgstcgaggcagaagatgytgsgrygt -3' |
| HBBK4-7D SEQ. ID: 15 | 5'-tagttccttgaccgaaagttgggggaaagctgtgaccat cttgacagtaatacrycscarcatcttctgc -3' |
| HBBK4-8D SEQ. ID: 16 | 5'-gagtcattctcgacttgcggccgctttgatctcgagtt tagttccttgaccgaaagt -3' |

The PCR for Scfv region amplifying was performed using by primer prepared according to FIG. 2. The PCR was performed as follows; pre-denaturation at 94° C. for 5 minutes, 1 cycle consists of denaturation at 94° C. for 30 sec, annealing at 59° C. for 1 minute and elongation at 72° C. for 30 second were repeated for 35 and post-elongation at 72° C. for 7 minutes. Resulting PCR products were isolated by QIAGEN Gel extraction kit.

3-4. Digestion and Purification of Insert.

To perform Sfi I digestion reaction, 85 µl of the mixture solution containing 8.5 µl of 10× buffer solution (Roche), 2 µl of SfiI (10 U/microliter, Roche), appropriate volume of purified ScFv product (1 µg) and distilled water was added to 85 µl of mineral oil and reacted together at 50° C. for 4 hours.

To perform Not I digestion reaction, 15 µl of the mixture solution containing 3.6 µl of 3 M NaCl, 1.5 µl of 10× buffer solution (Roche), 4 µl of Not I (10 U/0, Roche) and appropriate volume of distilled water was mixed thoroughly and reacted together at 37° C. for 4 hours. The reacted solution was subjected to phenol/chloroform extraction and isolation with Spin-column purification method.

3-5. Quantification of ScFv and Ligation to pCANTAB 5E Vector

The amount of ScFv was determined by electrophoresis: 25 ng of isolated ScFv were subjected to electrophoresis along with both 12.5 ng and 25 ng ScFv markers, and developed on 0.75 cm width of 1% agarose gel to compare therewith.

The insert was used in further ligation process and 50 µl of ligation mixture comprising 5 µl of 10×OPA buffer solution, 5 µl of pCANTAB 5E (50 ng/µl), 5 µl of 10 mM ATP, 2 µl of T4 DNA ligase (4 U/µl), 50 µl of distilled water and appropriate volume of BBK-4 ScFv gene fragment (150 ng) was reacted together at 16° C. for 1 hour. The solution was then reacted at 70° C. for 10 minutes to inactivate ligase and cooled in the ice for 5 minutes.

3-6. Confirmation of Transformation and Library Size

The product prepared in above-described ligation reactant was added to 1 ml of suitable TG1 cell and left alone in ice for 45 minutes. The mixture was incubated at 42° C. for 2 minutes and cooled in ice. 900 µl of LBG was added to 100 µl of the cooled solution and subjected to suspension incubation at the speed of 250 rpm. Those transformed cells were diluted and plating to obtain 6×10⁶ cfu of cell library.

3-7. Transformation into BBK-4 Recombinant Phage Antibody Library

900 µl of the cell library prepared in above-described step was added to 9.1 ml of 2×YT-G medium and subjected to suspension culture at the speed of 250 rpm at 37° C. for 1 hour. The supernatant was removed by centrifuging at the speed of 1000×g for 10 minutes to precipitate the cells. 10 ml of 2×YT-AK medium was added to the precipitated cells and subjected to overnight suspension culture at the speed of 250 rpm at 37° C. The suspension was centrifuged culture at the speed of 1000×g for 20 minutes to precipitate the cell again. The supernatant was filtered with 0.45 µm of filter paper and transferred to 50 ml of sterilized conical tube to store at 4° C. until it is subjected to panning.

3-8. PEG Precipitation of Recombinant Phage 2 ml of PEG/NaCl was added to BBK-4 recombinant phage antibody library, mixed with together thoroughly and incubated in ice for 60 minutes. The suspension was subjected to centrifugation at the speed of 1000×g at 4° C. for 20 minutes to precipitate the cell and remove the supernatant. 16 ml of 2×YT medium was added to the precipitates and mixed with together. The supernatant was filtered with 0.45 µm of filter paper and subjected to panning.

3-9. Panning for Selecting Antibody-Positive Recombinant Phage Antibody 4-1BB was diluted to 10 µg/ml with 0.05 M carbonate buffer solution (pH 9.6) and the solution was coated on 25 flasks at room temperature for 1 or 2 hours. The flask was washed with PBS solution three times, filled with blocking buffer solution to store at room temperature for one hour and washed again with PBS three times. 16 ml of precipitated recombinant phage with PEG was diluted with 14 ml of blocking buffer solution containing 0.01% sodium azide and reacted at room temperature for 15 minutes. 20 ml of diluted recombinant phage was poured to flask and reacted at 37° C. for 2 hours. The flask was washed with 50 ml of PBS solution 20 times and washed again with 50 ml of 0.1% PBS-T solution 20 times.

10 ml of grown-staged TG1 cell was poured in flask and incubated at 37° C. for 1 hour. 100 µl of the incubates was diluted to various concentration i.e., 1:10, 1:100, 1:1000 and subjected to plating on SOBAG plates by 100 µl per plate. The flask was subjected to overnight culture at 30° C. and the cfu of each plate was estimated. It has been confirmed that the library size was 9×10⁴ cfu.

3-10. Selection of Monoclone for Screening 880 colonies obtained after panning was inoculated into 96 well plates containing 200 µl of 2×YT-AG medium and subjected to overnight culture at the speed of 250 rpm at 30° C. 50 ml of 2×YT-AG medium containing M13K07 (2.5×10¹⁰ pfu) was distributed to new 96 well plates for 200 µl/well plate. The overnight incubates was inoculated into the plates by 40 µl/plate. The inoculated plates were subjected to suspension culture medium culture at the speed of 250 rpm at 37° C. and centrifugation at the speed of 1500×g for 20 minutes. The supernatant was further screened by ELISA method.

3-11. Screening through ELISA Method 4-1BB was diluted with 0.05 M carbonate buffer solution (pH 9.6) to 2 µg/mf and coated on ELISA plate by 100 µl/plate at room temperature for 1-2 hour. The plates were washed with PBS containing 0.01% tween 20 (PBS-T) three times. Each 200 µl of blocking buffer solution was added to each well, reacted at room temperature for one hour and the plate was washed with PBS-T buffer solution three times. 100 µl of recombinant phage antibody supernatant was added to the prepared plates and the equivalent amount of blocking buffer solution was mixed therewith to react at room temperature for 30 minutes. 200 μl of diluted recombinant phage antibody supernatant was added to antigen-coated wells and reacted at room temperature for 1 hour. After the reaction, the plates were washed with 0.01% PBS-T solution five times and diluted HRP/anti-M13 monoclonal conjugate with blocking buffer solution to 1:5000 by 200 μl/well to react at room temperature for 1 hour. The plates were washed with 0.01% PBS-T solution six times and 1×ABTS solution was added to each well by 200 μl/well to react at room temperature for 20 minutes. The clone showing more than 0.5 of absorbance has been regarded as positive clones through determining test of absorbance at 405 nm.

At the result of the screening, 162 positive clones were obtained and the nucleotide sequence of each clone was identified by sequencing analysis. Through the examination of overlapped sequences among the sequence, the sequences were divided into 54 groups having different sequence.

Example 4

Figure 3:
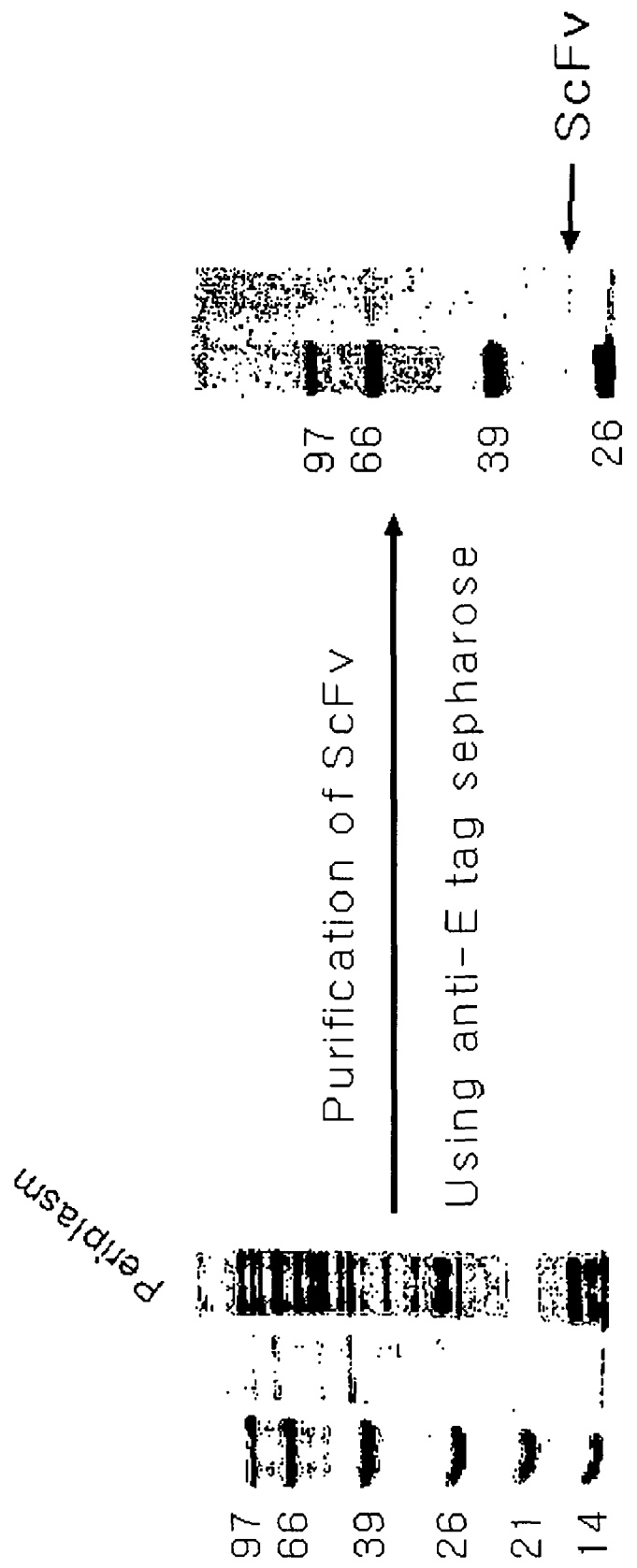
FIG. 3 depicts the purification procedure for purifying humanized BBK4 (HBBK4) ScFv using by anti-E tag sepharose.

Selection of HBBK4 Clone through the Functional Analysis on Humanized BBK4 (HBBK4) ScFv 4-1. Purification of BBK4 ScFv Each ScFv was purified using anti-E-Taq Sepharose column and the result was shown in FIG. 3.

4-2. Flow Cytometry using HBBK4 ScFv

Figure 4:
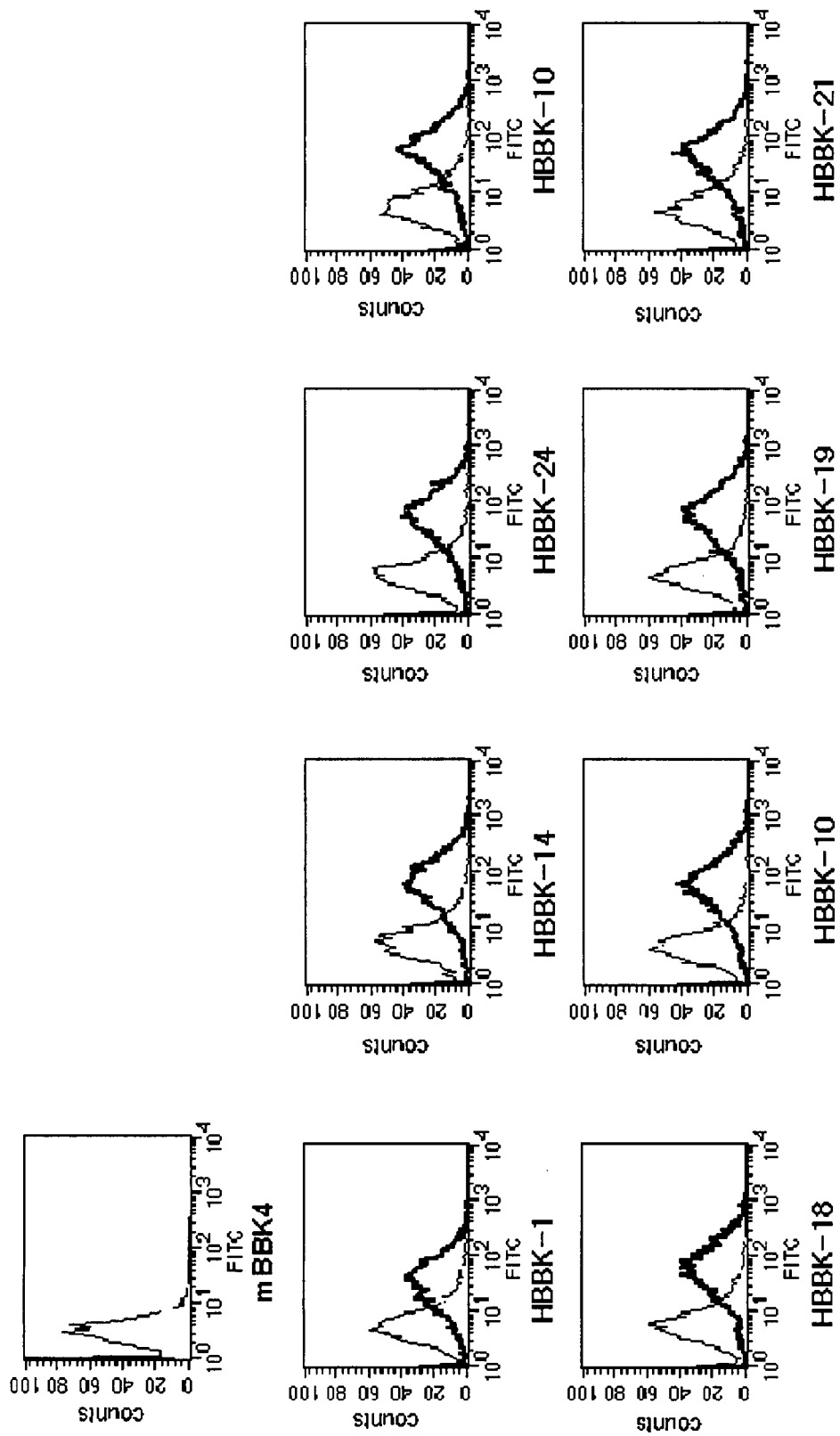
FIG. 4 depicts a flow cytometry analysis of HBBK4.

After the HBBK4 ScFv clones determined by ELISA screening, the clones were treated to Jurkat 8-1 cells expressing human 4-1BB to analyze the flow cytometry and the binding affinity of HBBK4 with human 4-1BB was identified. 2 μg of HBBK4 was added to 2×10$^5$ Jurkat 8-1 cells, reserved at 4° C. for 30 minutes and washed with PBS solution containing 0.1% BSA. Anti-human IgG-FITC was treated with secondary antibody to detect HBBK4. The stained cells were analyzed by flow cytometry analyzer (FACScan; BD Bioscience). FIG. 4 showed that several clones among HBBK4 clones recognize human 4-1BB similar to mouse BBK4.

4-3. Competitive ELISA

To identify each clone has original epitope such as mouse BBK4, following competitive ELISA adopted 4-1BB-GST as an antigen and the decreased ratio of HBBK4 ScFv binding affinity with the increased concentration of mouse BBK4 antibody prior to humanization was showed by the inhibition percentage represented by following Math Figure 1.

Inhibition ratio (%)=100×(non-competitive $OD_{405}$− competitive $OD_{405}$)/non-competitive $OD_{405}$.   Math Figure 1

Figure 5:
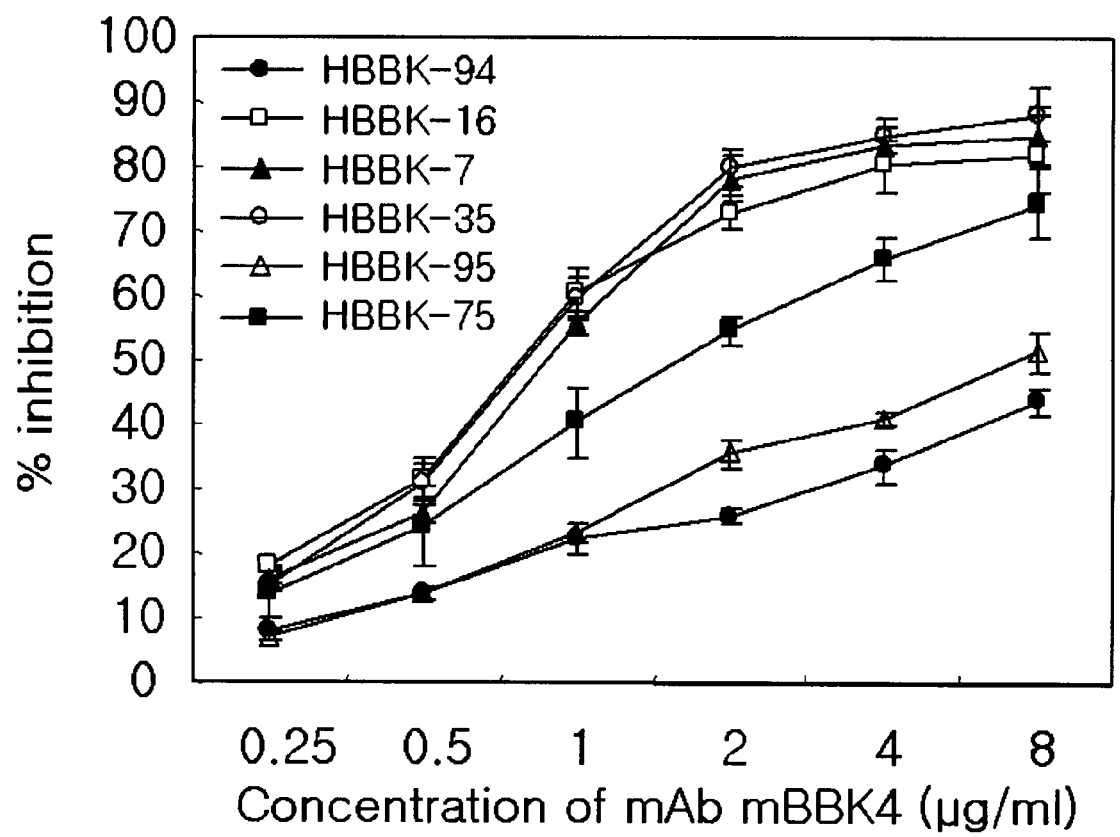
FIG. 5 depicts the result of competitive ELISA method.

As shown in FIG. 5, the inhibition ratio (%) was increased with the concentration of mouse BBK4 in a dose dependent manner therefore it has been proved that HBBK4 ScFv has similar epitope to that in original antibody, which strongly suggested that HBBK4 ScFv shows similar biological effect to that in mouse BBK4.

4-4. Linkage to Constant Region of Humanized ScFv

HBBK4 ScFv has VH, linker and VL regions linked together. To reform HBBK4 ScFv to original structure of antibody, i.e., H2L2 structure, leader sequence was linked to the VH region of BBK4 and the constant region of human IgG1 or IgG4 were linked thereto respectively. Both leader sequence and human kappa chain sequence were linked to kappa chain and the linkage of each fragment was performed through PCR method.

4-5. ELISA Using by H2L2

The completely humanized sequence to constant region was subcloned to pcDNA, a eukaryote expressing vectors, transfected into 293EBNA cells and serial analyses i.e., ELISA and western blotting analysis were performed using by the cell medium. 4-1BB-GST was used as an antigen for ELISA and each 50 numbers of transfectant medium was used therein. It has been confirmed that clone 75 showed highest expression rate among 50 clones which showed about 15 times higher than that of negative control as can be seen the result of ELISA method in Table 3.

TABLE 3

| Sample | Absorbance |
| --- | --- |
| HBBK4-75/pcDNA transfected 293 EBNA cultured supernatant | 1.935 |
| 293 EBNA cultured supernatant | 0.126 |

Figure 6:
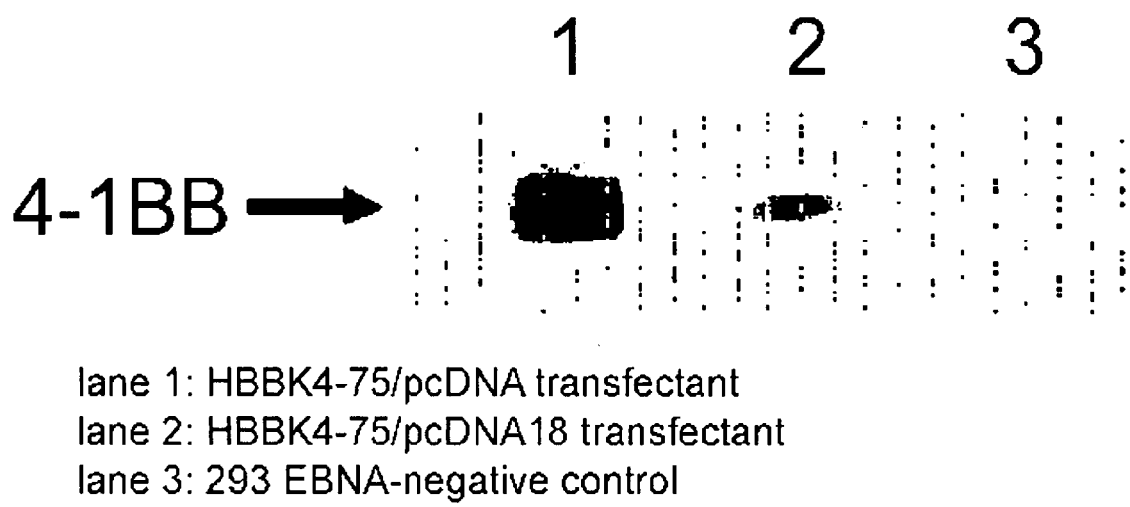
FIG. 6 depicts the result of western blotting using by H2L2 (lane 1: HBBK4-75/pcDNA transfectant, lane 2: HBBK4-75/pD18 transfectant, lane 3: 293 EBNA-negative control).
Figure 13:
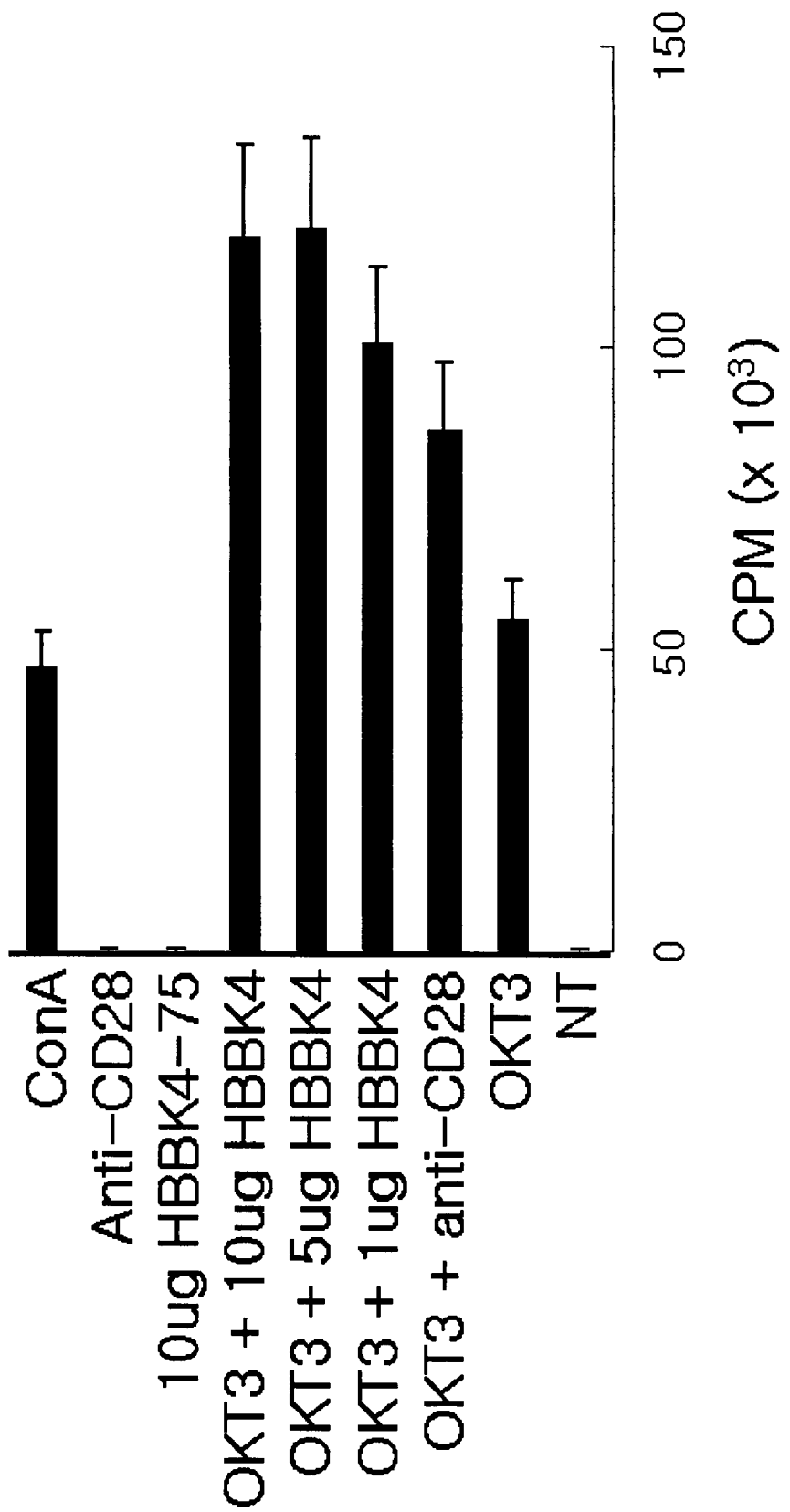
FIG. 13 represents the increasing effect of HBBK on the T cell proliferation.

Western blotting was performed using the antibody produced by selected clone 75 and it has been confirmed that completely humanized antibody HBBK4-75 clone showed potent affinity with human 4-1BB as shown in FIG. 6.

Example 5

Humanization of Agonistic Anti-Human 4-1BB (BBK4)

To apply the cancer treating method using by agonistic anti-4-1BB antibody to human body, the humanized antibody which minimize the adverse activity of antibody itself is necessary. The human antibody mostly similar to the heavy chain/light chain amino acids sequence of mouse BBK4 clone, namely agonistic anti-human 4-1BB antibody was screened and compared to perform humanization. Finally selected humanized agonistic anti-human 4-1BB antibody (HBBK4) was fused with two types of constant region, i.e., human IgG or IgG 4, which is designated as HBBK4-75G1 and HBBK4-75G4 respectively. The nucleotide sequence and amino acid sequence of finally synthesized HBBK4 antibody were shown in FIGS. 7-12 and SEQ. ID: 59 to SEQ. ID: 64.

Reference Example 1

Animal Model Test Using Agonistic Anti-Mouse 4-1BB Antibody 1-1. Antibody

Both of agonistic anti-rat 4-1BB and antagonistic anti-CTLA-4 antibody were isolated from rat ascites with protein G-column. Rat IgG used as a positive control was purchased from Sigma Co. and other antibodies used in cytometry analysis, i.e., anti-CD8-PE (53-6.7), anti-CD4-FITC (GK1.5), anti-CD8-FITC (53-6.7), anti-IFN-γ-PE (XMG1.2), anti-CD11c-PE (HL3), anti-NK1.1-PE (PK136) were from BD PharMingen Co.

1-2. Animal Model and Antibody Treatment

B16-F10 melanoma cancer cell line, a B16 melanoma mutant firstly reported by Hart (Francia G et al., *Cancer Res.* 56, 3855-3858, 1996) shows low antigenecity. 4×10$^5$ B16-F10 melanoma cells were subcutaneously injected to the back of mice to occur tumor. 200 μg of each agonistic anti-4-1BB (3H3 clone) and antagonistic anti-CTLA-4 antibody (9H10 clone) was injected into the rats with intraperitoneal administration of cancer cell line at five times per every 4 days for together or respectively. The size of tumor was determined at every 4 days according to the following Math Figure 2 and the survival rate of tumor-bearing mice was observed everyday.

The size of tumor=(width×length×height)×(π/6)    Math Figure 2

1-3. Isolation of Infiltrated Immune Cells from Tumor Tissue

The tumor tissue was isolated from agonistic anti-4-1BB, antagonistic anti-CTLA-4 or rat IgG-treated mice 18 days after the treatment. The isolated tumor tissue was mixed with HBSS to form single cell suspension and subjected to centrifugation by loading on upper surface of 63%/36% percoll gradient at the speed of 500×g at 45 minutes. After the centrifugation, white immune cell formed between 63% and 36% percoll was recovered and washed with RPMI 1640 twice to be used in following experiment.

1-4. Cell staining for flow cytometry

1 μg of 2.4G2 Fc blocker was added to the isolated immune cells from draining lymph node or tumor tissue and stored at 4° C. for 10 minutes. The cells were stained with anti-CD4-FITC+anti-CD8-PE and anti-CD8-FITC+anti-CD11c-PE, washed with PBS containing 0.1% BSA and analyzed with FACScan (BD Bioscience). The cells were surface-stained with anti-CD8-FITC for 30 minutes, fixed and permeabilized with 500 μl of Cytofix/Perm (BD PharMingen) for 20 minutes at room temperature, and washed with PermWash buffer (BD PharMingen) containing saponin. Above cells were intracellularly stained with anti-IFN-γ-PE for 30 minutes and analyzed with FACScan (BD Bioscience).

1-5. Counting the Number of Infiltrated Cd4+ and Cd8+ T Cell in Tumor Tissue

As described in the above, the infiltrated immune cells in tumor tissue were isolated using percoll and the cell number was counted by hematocytometer. The number of infiltrated CD4+ and CD8+ T cells in tumor tissue was calculated by following Math Figure 3.

Number of CD4+ and CD8+ T cell in tumor tissue=
(Number of total immune cell infiltrated in tumor cell)×Ratio of CD4+ or CD8+ T cell (%)/100.    Math Figure 3

1-6. Isolation of CD8c+CD11c+T Cell

CD8+ T cell and CD11c+CD8+ T cell were isolated from the delivered draining lymph node from arthritis-induced mice treated with agonistic anti-4-1BB or rat IgG respectively and the cells were isolated by MACS magnetic isolation system. The cells were incubated with suitable microbead-conjugated antibody to remove CD4+, F4/80+, CD40+, B220+ and DX5+, and further incubated with CD8-microbeads to isolate CD8+ T cell. The isolated CD8+ T cells were treated with CD11c-microbead and both of CD8+ CD11c+ and CD8+ CD11c− were further isolated therefrom using by LS isolation column (Miltenyi Biotech. Co. Ltd). Each isolated cell showed high purity of 96-98%.

1-7. Microarray and RT-PCR

CD8+ T, CD11c−CD8+ T, and CD11c+CD8+ T cells were isolated from the lymph node of B16-F10 tumor model 15 days after the tumor injection, and total RNA was extracted from each cells.

The extracted RNA was synthesized to cDNA using by in vitro reverse transcriptase and PCR was performed for each 0.5 μM primer using by 0.5 μl of cDNA. The expression level of each gene was compared using by gene-specific primers disclosed in Table 4, and SEQ. ID: 21 to SEQ. ID: 58.

TABLE 4

| Name | Orientaion | Primer |
|---|---|---|
| AnnexinA4 | Sense SEQ. ID: 21 | aatcaaccagacataccagc |
| | Anti-sense SEQ. ID: 22 | tcttcaaagcttccagatgt |
| Klrg1 | Sense SEQ. ID: 23 | ctttgcaatggtggctttt |
| | Anti-sense SEQ. ID: 24 | ctccagccatcaatgttc |
| CD68 Ag | Sense SEQ. ID: 25 | gcatatctgttttgaatccc |
| | Anti-sense SEQ. ID: 26 | ccttagagagagcaggtcaa |
| THRI13 | Sense SEQ. ID: 27 | gtgatgaccaccgtactctt |
| | Anti-sense SEQ. ID: 28 | gcattgactactcggatagc |
| NKG2 | Sense SEQ. ID: 29 | cgattcacccttaacacatt |
| | Anti-sense SEQ. ID: 30 | gctggaattttgagacaaac |
| TGF-β1 | Sense SEQ. ID: 31 | ttgacgtcactggagttgta |
| | Anti-sense SEQ. ID: 32 | aatagttggtatccagggct |
| PRP1 | Sense SEQ. ID: 33 | cagcattaccacaagaatga |
| | Anti-sense SEQ. ID: 34 | cccacattccagaagattta |
| IL-1R II | Sense SEQ. ID: 35 | cgatgcaggctattacagat |
| | Anti-sense SEQ. ID: 36 | atcaaaaatcagcgacactt |
| Granzyme B | Sense SEQ. ID: 37 | cccaggcgcaatgctaat |
| | Anti-sense SEQ. ID: 38 | ccaggataagaaactcga |
| GAPDH | Sense SEQ. ID: 39 | gaacgggaagcttgtcat |
| | Anti-sense SEQ. ID: 40 | ctaagcagttggtggtgc |
| Tim-3 | Sense SEQ. ID: 41 | atccagcagataccagctaa |
| | Anti-sense SEQ. ID: 42 | tccattgttattatggaggg |
| IL-4 ig 1 | Sense SEQ. ID: 43 | gtatcttcactttccgggat |
| | Anti-sense SEQ. ID: 44 | gaggtagaagaagccctcc |
| pleckstrin | Sense SEQ. ID: 45 | actgaatctggagaaggaca |
| | Anti-sense SEQ. ID: 46 | ttcagtaaacatccctgctt |
| TIP2 | Sense SEQ. ID: 47 | aaagcaaagcaaatgaagag |
| | Anti-sense SEQ. ID: 48 | tcagtggaggaatggtaatc |
| LAG3 | Sense SEQ. ID: 49 | gtctccatcacgtacaacct |
| | Anti-sense SEQ. ID: 50 | cacaaatctttcctttccag |

TABLE 4-continued

| Name | Orientaion | Primer |
| --- | --- | --- |
| Klrg2-A1 | Sense SEQ. ID: 51 | tcctccagagaaactcattg |
|  | Anti-sense SEQ. ID: 52 | tacagttttggaaatgcag |
| CD27 | Sense SEQ. ID: 53 | gctgaatctcacagttcctc |
|  | Anti-sense SEQ. ID: 54 | ccagtgtcacctggatatg |
| Perforin | Sense SEQ. ID: 55 | gtcacgtcgaagtacttg |
|  | Anti-sense SEQ. ID: 56 | atggctgatagcctgtct |
| IFN-γ | Sense SEQ. ID: 57 | aacgctacacactgcatc |
|  | Anti-sense SEQ. ID: 58 | gccgtggcagtaacagcc |

Experimental Example 1

Characteristic of Humanized Agonistic Anti-Human 4-1BB (HBBK4)

To identify the characteristic of HBBK4 antibody, T cell was isolated from human peripheral blood. The isolated cells were treated with anti-CD3 mAb (OKT3) to induce T cell activation and humanized anti-4-1BB antibody (HBBK4-75) in a dose dependent manner to determine the proliferation rate of the cell. The activity of T cell induced by OKT3 was increased in a dose dependent manner whereas the groups treated with HBBK4-75 or anti-CD28 antibody only did not induce T cell activation. (FIG. 7).

Accordingly, it has been confirmed that finally prepared humanized anti-human 4-1BB antibody, HBBK4-75 recognizes as well as co-stimulates human 4-1BB as an agonistic antibody.

Experimental Example 2

Combined Cancer Therapy Using Agonistic Anti-4-1BB and Antagonistic Anti-CTLA-4 Antibody To predict the treating activity of agonistic HBBK4 in Clinical study, animal model test using B16-F10 melanoma tumor cell injected animal model performed using by rat agonistic anti-4-1BB antibody together with antagonistic anti-CTLA-4 antibody well known to show potent anti-cancer activity to maximize their therapeutic efficacy and enhance T cell response.

Figure 14:
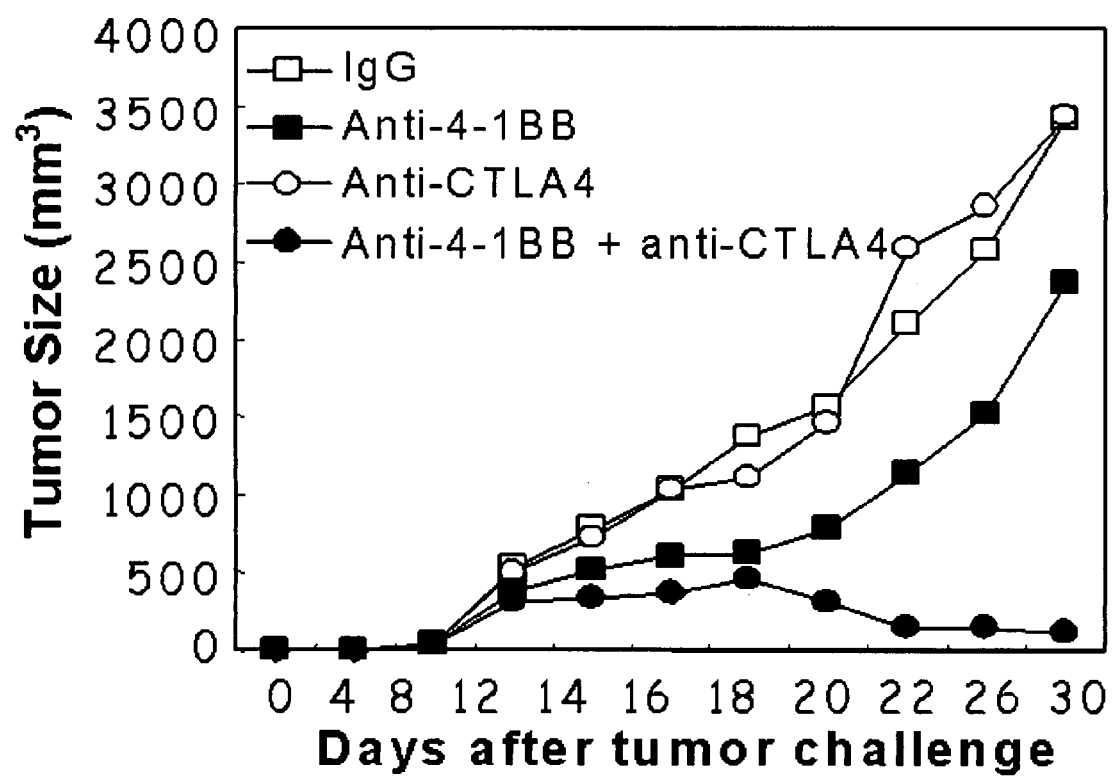
FIG. 14 depicts the change of tumor size in multi-therapy of melanoma using by combined mixture of agonistic anti-4-1BB and antagonistic anti-CTLA-4 antibody.
Figure 15:
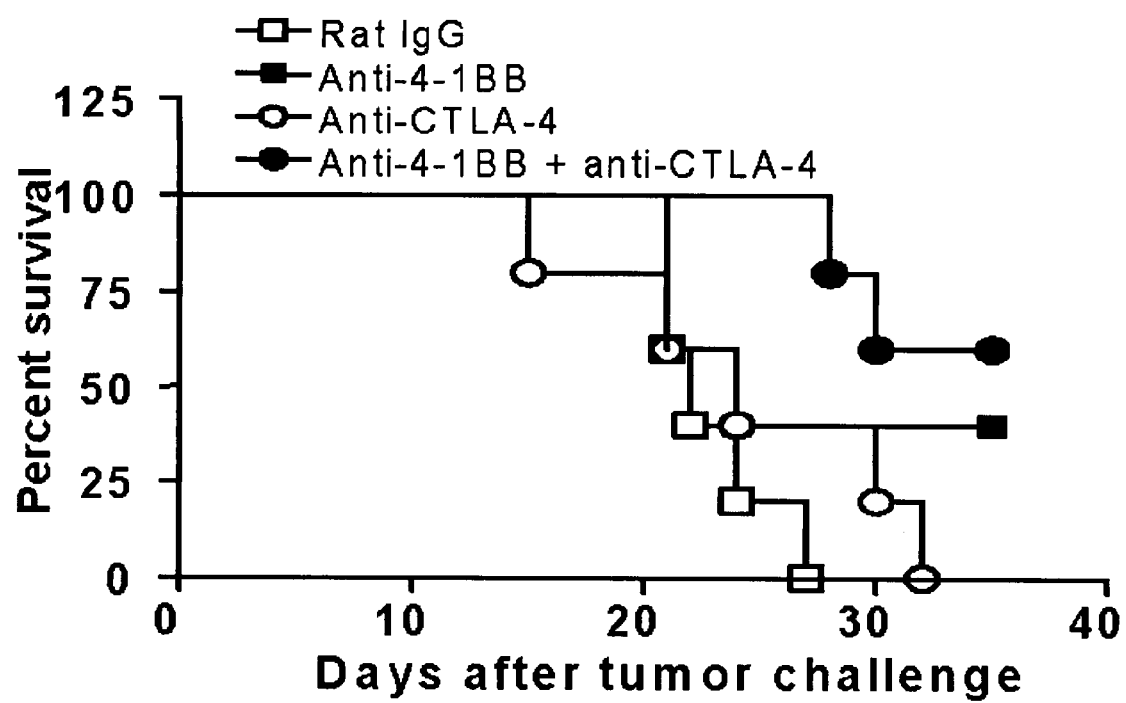
FIG. 15 depicts the change survival rate of rat in multi-therapy of melanoma using by combined mixture of agonistic anti-4-1BB and antagonistic anti-CTLA-4 antibody.

To determine each and combined anti-cancer therapeutic activity of agonistic anti-4-1BB and/or antagonistic anti-CTLA-4 antibody, $4 \times 10^5$ B16-F10 melanoma cells were subcutaneously injected into the back of six-weeks old C57BL/6 mice together with 200 μg of each antibody five times every four days and rat IgG antibody was treated as a control group. The tumor size in treatment group with only agonistic anti-4-1BB antibody was a rather smaller than that of control group and that in treatment group with only antagonistic anti-CTLA-4 antibody was similar to that in control group. On the contrary, the group treated with both of them showed slow cancer growth till $20^{th}$ days after the test and the size of tumor was decreased slowly after then (FIG. 14). At $35^{th}$ day after the injection of tumor cells, the survival rate of each group showed 80% in treatment group with agonistic anti-4-1BB antibody, 40% in treatment group with antagonistic anti-CTLA-4 antibody, 100% in the treatment with both of them while the lethal rate in control group showed 100% in $30^{th}$ day (FIG. 15).

Experimental Example 3

CD8+ T Cell Increase and CD11c+CD8+ T Cell Production Stimulated by 4-1BB

Figure 16:
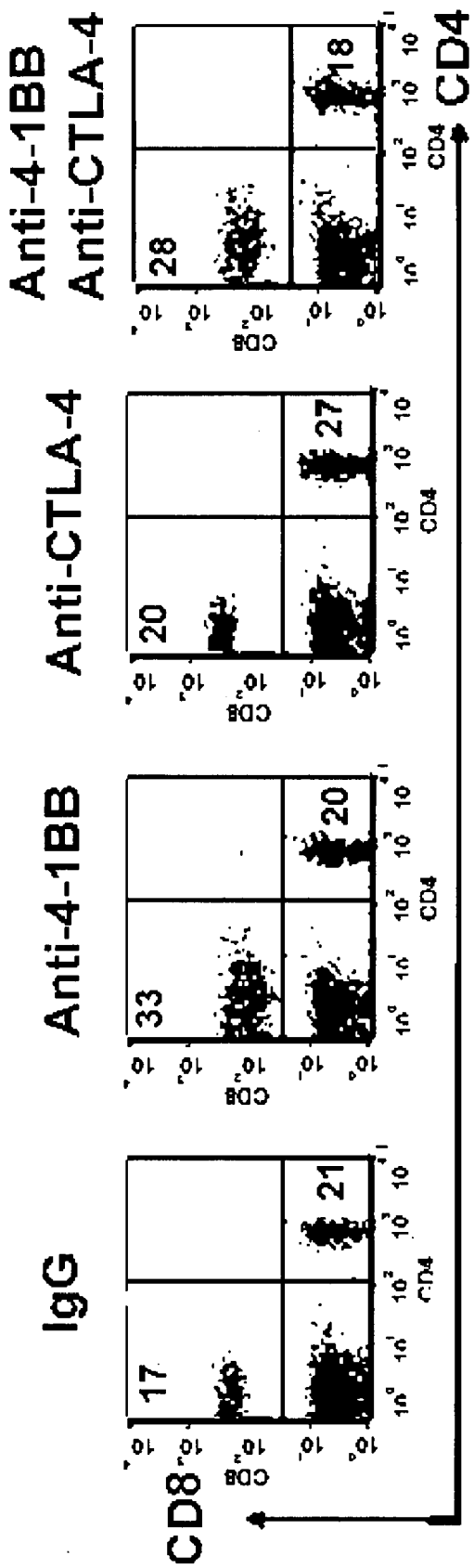
FIG. 16 depicts the analysis of flowcytometry stained with anti-CD4-FITC+anti-CD8-PE.
Figure 17:
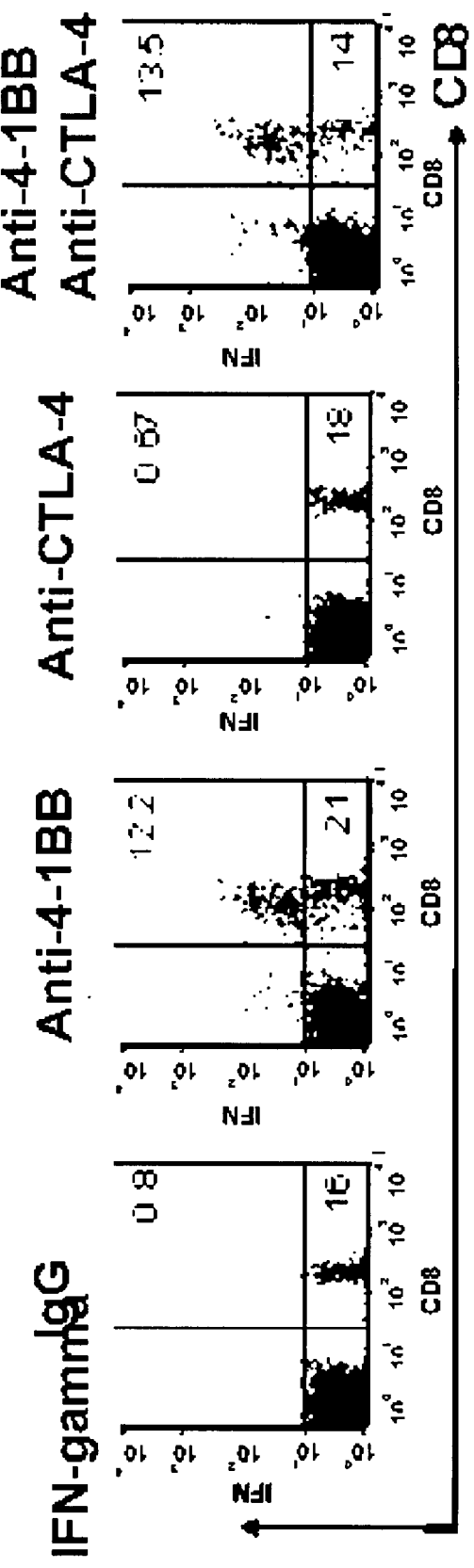
FIG. 17 depicts the analysis of flowcytometry stained with anti-CD8-FITC+anti-WN-γ-PE.

To analyze the combined treating activity of agonistic anti-4-1BB and antagonistic anti-CTLA-4 antibody, inguinal LN, i.e., draining lymph node was isolated from the mice in each group to investigate the proportion of each cell population. The ratio of $CD8_+T$ cells necessary in removing tumor cell were increased to twice and the IFN-γ expression rate of CD8+ T cells were increased to more than five times when agonistic anti-4-1BB antibody was treated (FIG. 16 and FIG. 17). Both of the ratio of CD8+ T cells and IFN-γ expression rate showed no significant difference from control group when antagonistic anti-CTLA-4 antibody was treated, however both of CD4+ and CD8+ T cell showed increasing tendency (FIGS. 16 and 17). The number of CD8+ T cells in treatment group with both of them were increased with similar to that in treatment group with anti-4-1BB, however the IFN-γ expression rate of CD8+ T cell was sharply increased to the extent about 30% among total CD8+ T cells expressed IFN-γ (FIG. 16 and FIG. 17).

Figure 18:
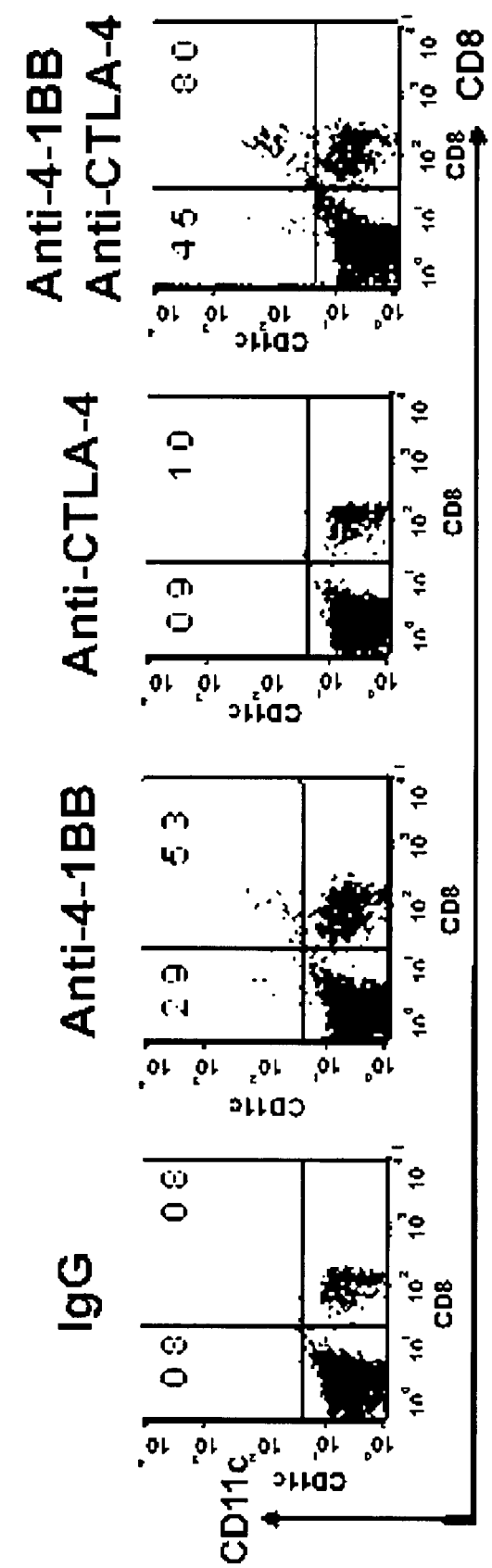
FIG. 18 depicts the analysis of flowcytometry stained with anti-CD8-FITC+anti-CD11c-PE.

There has been reported that the administration of agonistic anti-4-1BB antibody could treat and inhibit collagen induced arthritis (CIA) disease in mice, of which activity is mediated by CD11c+CD8+ T cell (Seo S K et al., Nat. Med., 10, pp 1088-1094, 2004). Based on those result, the present inventors have studied to confirm whether the cancer cell therapy using by agonistic anti-4-1BB antibody produces the same cell population or not and finally confirmed the presence of CD11c+CD8+ T cell by staining the isolated cells from draining lymph node with fluorescence-conjugated anti-CD11c and anti-CD8 antibody. Identical cell groups were formed when anti-4-1 BB antibody was administrated in animal tumor model and 36% of CD8+ cells were CD11c+CD8+ T cells. The ratio of identical cell groups was further increased to the extent that 50% CD8+ T cell expressed CD11c in case of combined therapy (FIG. 18).

Those results showed that the treatment of agonistic anti-4-1BB antibody increased population of CD8+ T cells and expression of IFN-γ as well as anti-CTLA-4 antibody maximized those activity more. Additionally, it is suggested that CD11c+CD8+ T cell is involved in the cancer therapy using anti-4-1BB antibody.

Experimental Example 4

Infiltration of CD11c+CD8+ T Cell into Tumor by Agonistic Anti-4-1BB

Figure 19:
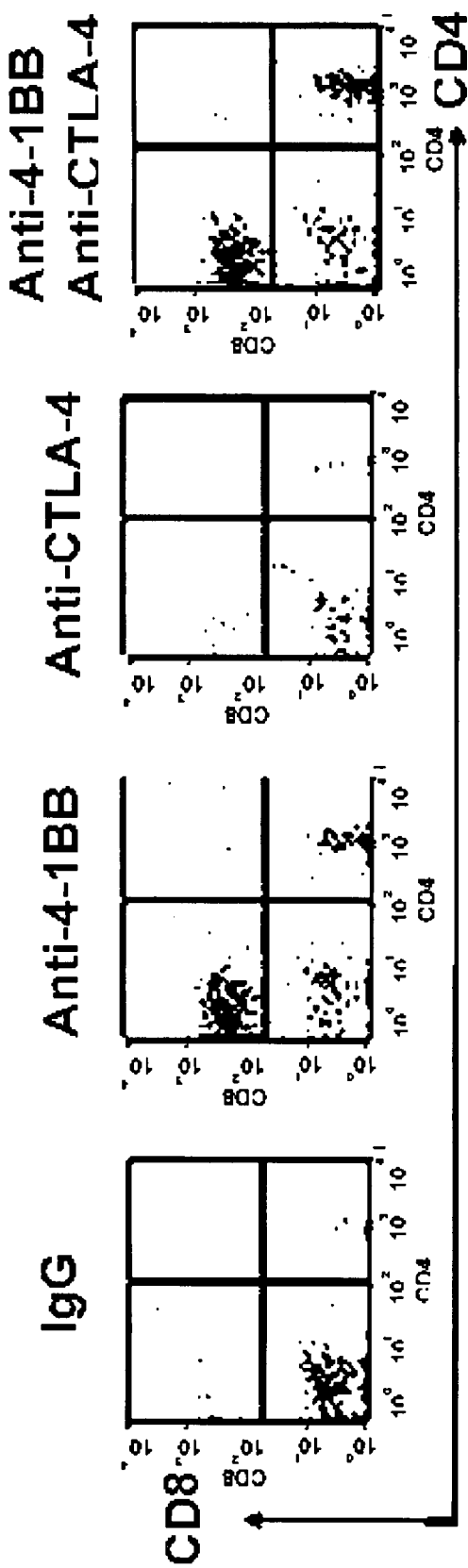
FIG. 19 shows the infiltration of CD11c+CD8+ T cell into tumor tissue resulting from the administration of agonistic anti-4-1BB, of which cells are stained with anti-CD4-FITC+anti-CD8-PE.
Figure 20:
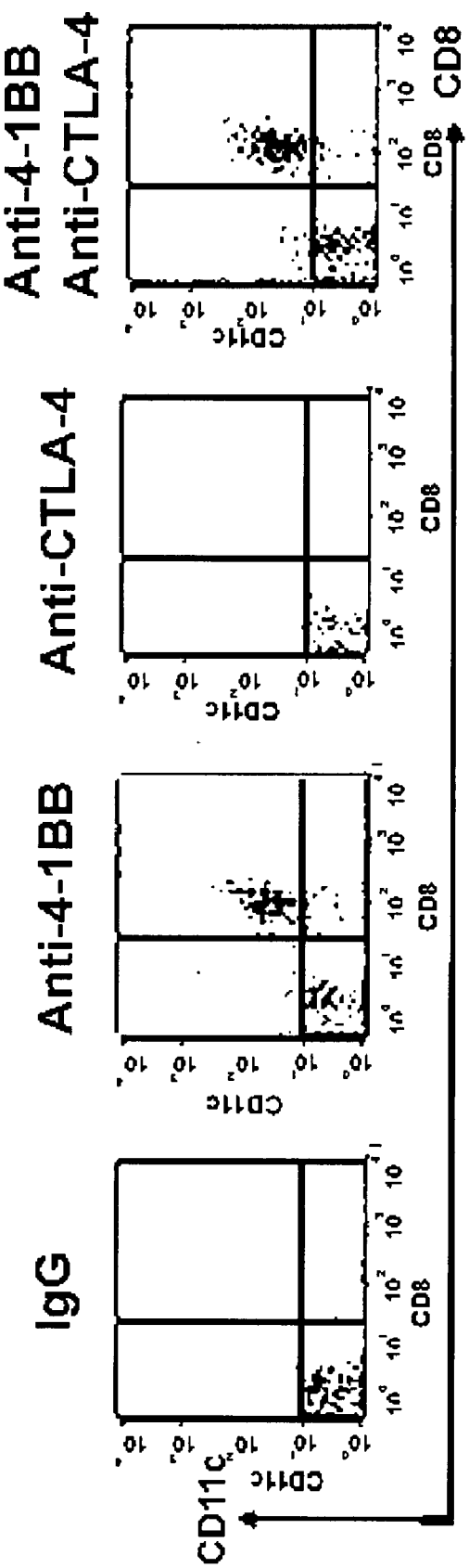
FIG. 20 shows the infiltration of CD11c+CD8+ T cell into tumor tissue resulting from the administration of agonistic anti-4-1BB, of which cells are stained with anti-CD8-FITC+anti-CD11c-PE.
Figure 21:
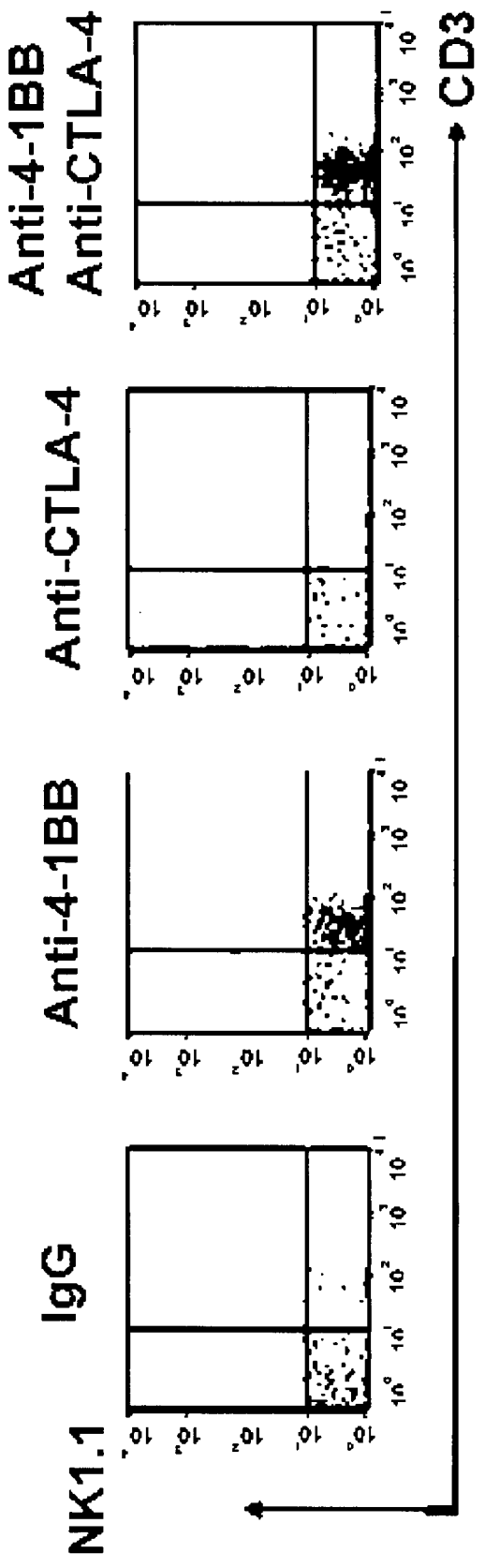
FIG. 21 shows the infiltration of CD11c+CD8+ T cell into tumor tissue resulting from the administration of agonistic anti-4-1BB, of which cells are stained with anti-CD3-FITC+anti-NK1.1-PE.

To confirm whether the increase of CD8+ T cells and IFN-γ as well as the formation of CD11c+CD8+ T cells are involved with the proliferation of cancer cell directly or not, the proportion and characteristic of each cell group were analyzed by isolating immune cell from tumor. The B16-F10 melanoma cells together with 200 μg of each antibody, i.e., rat IgG, ant-4-1BB, anti-CTLA-4 or anti-4-1BB+anti-CTLA-4 were injected subcutaneously into the rats every four days. The tumor isolated at $18^{th}$ day after the injection of cancer cells was centrifuged by 36%/63% percoll. After investigation of the ratio of CD4+/CD8+ T cell among the cells, less than 5% CD4+/CD8+ T cells presented in control group treated with only rat IgG while the infiltration ratio of CD8+ T cells and CD4+ T cells in test group treated with anti-4-1BB were increased to 62% and 13%. The treatment group with antagonistic anti-CTLA-4 antibody showed similar level to that of control group and the treatment group with both of them showed similar level to that in treatment group with anti-4-1BB antibody (FIG. 19). It has been confirmed that the CD11c+CD8+ T cell found in draining lymph node was also found in tumor and more than 90% CD8+ T cell infiltrated into tumor was CD11c+CD8+ T cell (FIG. 20). NK cell was also involved with cancer cell removal. Additionally, we have studied to determine the ratio of NK cell in tumor to confirm whether those cell groups are involved in the cancer inhibiting process by agonistic anti-4-1BB antibody or not and found that the increase of NK cell in any test groups did not show (FIG. 21).

Figure 22:
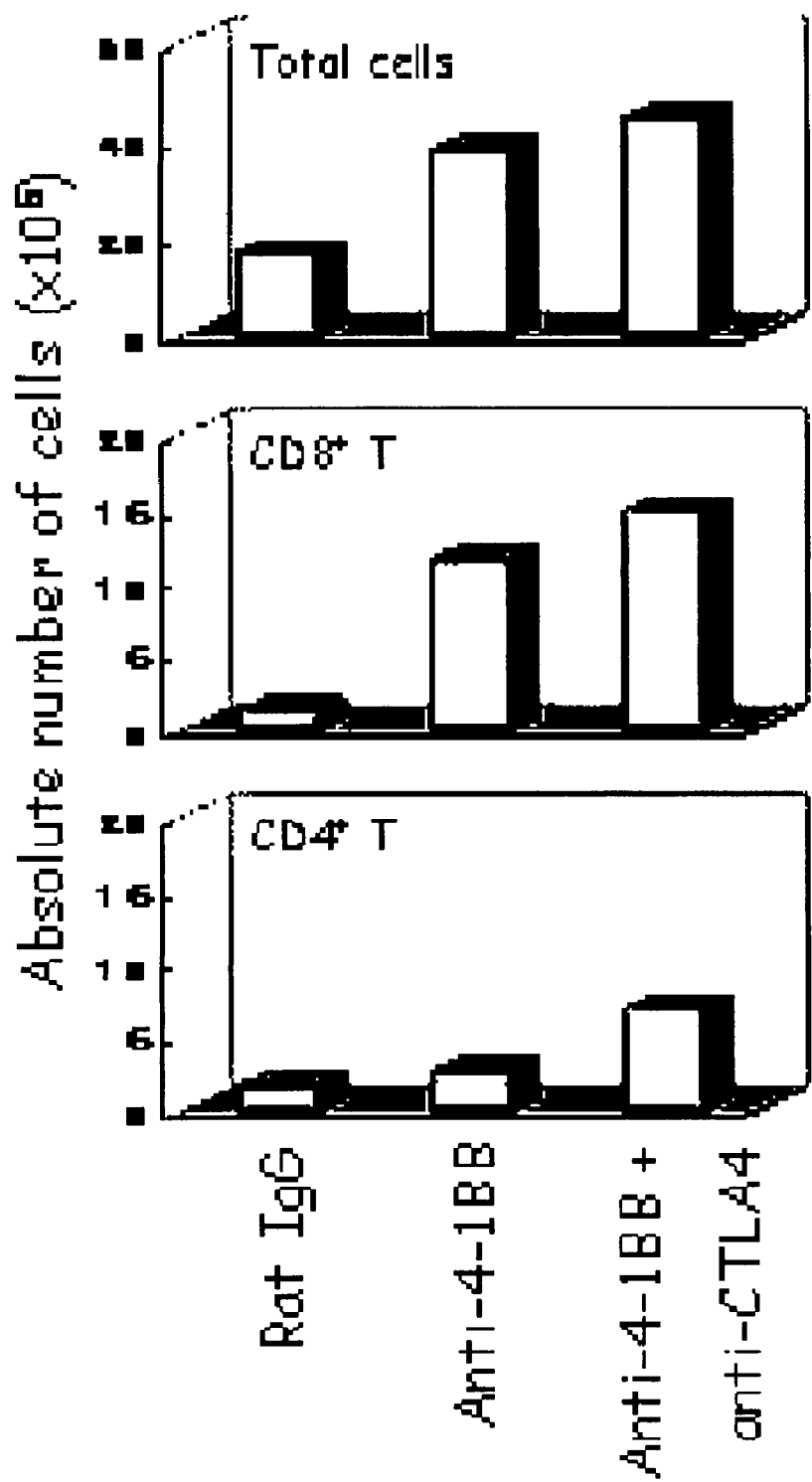
FIG. 22 shows the result of calculating an absolute number of CD4+/CD8+ T cells among the recovered cells from each tumor tissue in flow cytometry analysis.

The number of cells infiltrated into tumor in treatment groups with agonistic anti-4-1BB and both of them was increased to about twice and 2.5 times respectively (FIG. 22). The number of CD8+ T cell in treatment group with anti-4-1BB and both of them was increased to about 10 times and 15 times respectively when the number of CD4+/CD8+ T cell in tumor was calculated from the flow cytometry analysis. The number of CD4+ T cell in treatment group with anti-4-1BB was a rather increased whereas that in treatment group with both of them was increased to 4 times (FIG. 22).

Those results suggested that the treatment of agonistic anti-4-1BB antibody led to the differentiation and proliferation of CD11c+CD8+ T cells, and the cells were infiltrated into tumor and caused the inhibition of cancer cell proliferation. Anti-CTLA-4 antibody maximizes the anti-cancer potency of anti-4-1BB antibody and NK cell was not involved with those processes.

Experimental Example 5

Gene Expression Distribution of CD11c+CD8+ T Cell

To analyze the characteristics of CD11c+CD8+ T cell formed by agonistic anti-4-1BB antibody and confirm which gene expression effects on cancer cell proliferation. The gene expression of CD11c+CD8+ T cell and CD8+ T cell of anti-4-1BB– or rat IgG-treted mice was compared. There have been reported that the treatment of agonistic anti-4-1BB results in inhibiting autoimmune disease and the treatment activity is mediated by CD11c+CD8+ T cell. Accordingly, DNA array was performed using by the cells isolated from CIA (Collagen induced arthritis) model, i.e., CD11c+CD8+ T cell in anti-4-1BB antibody-treated mice and CD8+ T cell in rat IgG-treated mice and the gene expression of CD11c+ CD8+ T cell formed in cancer model was determined based on such result.

Collagen was administrated to mice induce arthritis and 200 μg of each rat IgG or anti-4-1BB antibody was intraperitoneally injected five times every two days simultaneously. The draining lymph nodes of each mice, i.e., inguinal and iliac LN were delivered to isolate CD11c+CD8+ T cell in anti-4-1BB antibody-treated mice and CD8+ T cell in rat IgG-treated mice at $14^{th}$ day after final administration of antibody. RNA was extracted from such cells and the gene expression difference between two cells was analyzed using by Affimatrix microarray system. CD11c+CD8+ T cell formed by 4-1BB stimulus showed high expression at about 220 gene and the gene expression involved with T cell effector function, apoptosis, anti-apoptosis and cell adhesion and migration in CD11c+CD8+ T cell was increased as shown in Table 5.

Collagen was administrated to rats induce arthritis and 200 μg of each rat IgG or anti-4-1BB antibody was intraperitoneally injected five times every two days simultaneously. The draining lymph nodes of each rat, i.e., inguinal and iliac LN was delivered to isolate CD11c+CD8+ T cell in anti-4-1BB antibody treated rat and CD8+ T cell in rat IgG treated rat CD8+ T cell at $12^{th}$ day after collagen immunization. RNA was extracted from such cells and the gene expression difference between two cells was analyzed using by Affimatrix microarray system. The genes showing relatively high expression among the gene expression involved with T cell effector function, apoptosis, anti-apoptosis and cell adhesion and migration in CD11c+CD8+ T cell was shown in Table 5.

TABLE 5

| gene | fold |
|---|---|
| T cell effector functions | |
| annexin A4 | 3.20 |
| interleukin-four induced gene 1 | 2.87 |
| Scyb9 | 2.78 |
| small inducible cytokine A3 | 2.66 |
| Klrg1 | 2.47 |
| interleukin 10 receptor, alpha | 2.45 |
| T cell immunoglobulin mucin-3 | 2.38 |
| peptidoglycan recognition protein | 2.32 |
| interferon g | 2.30 |
| CD68 antigen | 2.30 |
| natural killer cell protein group 2-A1 | 2.27 |
| pleckstrin | 2.12 |
| annexin A2 | 2.07 |
| MHC class II antigen IE alpha (H2-Ea) | 2.05 |
| CD27L | 2.00 |
| natural killer cell protein group 2-A2 | 1.95 |
| MHC class II H2-IA-beta chain | 1.94 |
| NKG2 | 1.92 |
| Ct1a2a | 1.88 |
| Ct1a2b | 1.87 |
| MHC class II H2-IA-beta chain | 1.84 |
| 4-1BB | 1.77 |
| pleckstrin 1 small isoform | 1.76 |
| transmembrane 7 superfamily member 1 | 1.72 |
| neurocalcin delta | 1.68 |
| metallopeptidase | 1.67 |
| lymphotactin | 1.60 |
| thyroid hormone receptor interactor 13 | 1.55 |
| C1qc | 1.49 |
| interleukin 1 receptor, type II | 1.44 |
| CD74 | 1.40 |
| CD38 antigen | 1.38 |
| serinethreonine kinase 5 | 1.37 |
| Brca1 | 1.35 |
| hyaluronan receptor RHAMMV5 | 1.34 |
| lymphocyte-activation gene 3 | 1.25 |
| B lymphocyte induced maturation protein | 1.25 |
| Mac-2 antigen | 1.20 |
| lectin, galactose binding, soluble 1 | 1.19 |
| CD9 antigen | 1.16 |
| RHAMM | 1.15 |
| CD38 antigen | 1.13 |
| B-cell CLLlymphoma 7C | 1.05 |
| Apoptosis | |
| Fas antigen ligand | 3.03 |
| calsenilin | 2.76 |
| granzyme K | 2.58 |
| granzyme B | 2.20 |
| Caspase 3 | 1.93 |
| hemopoietic-specific early-response protein | 1.84 |

TABLE 5-continued

| gene | fold |
| --- | --- |
| programmed cell death 1 | 1.53 |
| caspase 1 | 1.42 |
| Anti-apoptosis | |
| serine protease inhibitor 12 | 2.07 |
| serine protease inhibitor 6 | 1.92 |
| baculoviral IAP repeat-containing 5 | 1.66 |
| cystatin C | 1.62 |
| Cell adhesion and migration | |
| CD11c | 2.67 |
| MCP-1 | 2.49 |
| chemokine (C-C) receptor 2 | 2.38 |
| C-C chemokine receptor 5 | 2.07 |
| MIP-1 alpha receptor | 2.03 |
| catenin alpha 1 | 1.23 |
| chemokine-like factor super family 7 | 1.09 |
| CD166 | 1.07 |

Figure 23:
FIG. 23 shows the level and distribution of gene expression of CD11c+CD8+ T cell.

Simultaneously with the injection of B16-F16 melanoma cell line, 200 μg of anti-4-1BB or rat IgG was injected to the mice five times every two days and the draining lymph nodes of each mice, i.e., inguinal LN was delivered to isolate CD11c+CD8+ T cell and CD8+ T cell at 4$^{th}$ day after final administration of antibody. RNA was extracted from the isolated cells to synthesize cDNA and the increased gene expression shown in Table 5 was analyzed. The gene expression of Tim3, IL4 ig1, IL-1R II, THRI13, LAG3, pleckstrin, TIP2, K1rg2-A1, PRP1, Annexin A4, TGF-β, K1rg1, CD68Ag, NKG2, IFN-γ, perforin, granzyme B was determined by RT-PCR and most of gene expression excluding PRP1 and perforin was found to be increased (FIG. 23). Those results indicated there were no significant differences of CD11c+ CD8+ T cells formed by anti-4-1 BB treatment in between the autoimmune disease model and the cancer model. CD11c+ CD8+ T cells isolated from cancer model showed high level of gene expression in respect to IFN-γ and granzyme B necessary in removal of cancer cell, which showed that those cell groups are effective in cancer cell removal. The expression of K1rg1 showing differentiated status reinforced with CTL effector function rather than T cell proliferation showed high level in CD11c+CD8+ T cell and besides the K1rg1, the expression of annexin A4 involved in anti-apoptosis in T cell, CD27 and THRI13, a co-stimulating molecules of T cell, Tim-3 gene and LAG-3 gene involved with the regulation of T cell function were found to be highly increased. Those results suggest that CD11c+CD8+ T cells are not a cell showing CTL function simply but a cell which could control immune response.

Hereinafter, the formulating methods and kinds of excipients will be described, but the present invention is not limited to them. The representative preparation examples were described as follows.

| Preparation of injection | |
| --- | --- |
| HBBK4 | 100 mg |
| Sodium metabisulfite | 3.0 mg |
| Methyl paraben | 0.8 mg |
| Propyl paraben | 0.1 mg |
| Distilled water for injection | optimum amount |

Injection preparation was prepared by dissolving active component, controlling pH to about 7.5 and then filling all the components in 20 ml ample and sterilizing by conventional injection preparation method.

| Preparation of powder | |
| --- | --- |
| HBBK4 | 500 mg |
| Corn Starch | 100 mg |
| Lactose | 100 mg |
| Talc | 10 mg |

Powder preparation was prepared by mixing above components and filling sealed package.

| Preparation of tablet | |
| --- | --- |
| HBBK4 | 200 mg |
| Corn Starch | 100 mg |
| Lactose | 100 mg |
| Magnesium stearate | optimum amount |

Tablet preparation was prepared by mixing above components and entabletting.

| Preparation of capsule | |
| --- | --- |
| HBBK4 | 100 mg |
| Lactose | 50 mg |
| Corn starch | 50 mg |
| Talc | 2 mg |
| Magnesium stearate | optimum amount |

Tablet preparation was prepared by mixing above components and filling gelatin capsule by conventional gelatin preparation method.

| Preparation of liquid | |
| --- | --- |
| HBBK4 | 1000 mg |
| Sugar | 20 g |
| Polysaccharide | 20 g |
| Lemon flavor | 20 g |

Liquid preparation was prepared by dissolving active component, and then filling all the components in 1000 ml ample and sterilizing by conventional liquid preparation method.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

INDUSTRIAL APPLICABILITY

As described in the present invention, the composition comprising inventive HBBK4 antibody of the present invention showed inhibition effect on cancer cell proliferation caused by increase of CD11c+CD8+ T cell population and IFN-γ expression. Accordingly, it can be useful in the prevention or treatment of cancer diseases and in providing an immune therapy of cancer disease without adverse response.

The invention claimed is:

1. A pharmaceutical composition comprising the combined mixture of a humanized anti-4-1 BB antibody (HBBK4) comprising an amino acid sequence encoded by at least one nucleotide sequence selected from the group consisting of SEQ. ID: 59, SEQ. ID: 61 and SEQ. ID: 63; and anti-CTLA-4 antibody for treating cancer disease through the synergic inhibition effect on cancer cell proliferation as an effective ingredient, together with a pharmaceutically acceptable carrier.

2. The pharmaceutical composition of claim 1 wherein said composition contains the humanized anti-4-1BB antibody (HBBK4) between 0.1 to 50% by weight based on the total weight of composition.

3. A pharmaceutical composition comprising the combined mixture of a humanized anti-4-1 BB antibody (HBBK4) comprising at least one amino acid sequence selected from the group consisting of SEQ. ID: 60, SEQ. ID: 62 and SEQ. ID: 64; and anti-CTLA-4 antibody for treating cancer disease through the synergic inhibition effect on cancer cell proliferation as an effective ingredient, together with a pharmaceutically acceptable carrier.

4. The pharmaceutical composition of claim 3 wherein said composition contains the humanized anti-4-1BB antibody (HBBK4) between 0.1 to 50% by weight based on the total weight of composition.

* * * * *

SEQUENCE LISTING

<160> NUMBER OF SEQ ID NOS: 80

<210> SEQ ID NO 1
<211> LENGTH: 18
<212> TYPE: DNA
<213> ORGANISM: Artificial Sequence
<220> FEATURE:
<223> OTHER INFORMATION: Linker primer containing XhoI site

<400> SEQUENCE: 1
ctcgagtttt ttttttt                                                      18

<210> SEQ ID NO 2
<211> LENGTH: 71
<212> TYPE: DNA
<213> ORGANISM: Artificial Sequence
<220> FEATURE:
<223> OTHER INFORMATION: HBBK4-1U: BBK4 ScFv combinational primer

<400> SEQUENCE: 2
actgcggccc agccggccat ggcccaggtg cagctgcagc agtctggggc tgaagtarwa       60
aagcctgggg c                                                            71

<210> SEQ ID NO 3
<211> LENGTH: 70
<212> TYPE: DNA
<213> ORGANISM: Artificial Sequence
<220> FEATURE:
<223> OTHER INFORMATION: HBBK4-1D: BBK4 ScFv combinational primer

<400> SEQUENCE: 3
agtagctgct gaaggtgtag ccagaagcct tgcaggaaas cttcactgaa gccccaggct       60 ttwytacttc                                                              70

<210> SEQ ID NO 4
<211> LENGTH: 70
<212> TYPE: DNA
<213> ORGANISM: Artificial Sequence
<220> FEATURE:
<223> OTHER INFORMATION: HBBK4-2U: BBK4 ScFv combinational primer

<400> SEQUENCE: 4
tacaccttca gcagctactg gatgcactgg gtgargcagg cacctggaca aggccttgag       60
tggattggag                                                              70

<210> SEQ ID NO 5
<211> LENGTH: 70
<212> TYPE: DNA
<213> ORGANISM: Artificial Sequence
<220> FEATURE:
<223> OTHER INFORMATION: HBBK4-2D: BBK4 ScFv combinational primer

<400> SEQUENCE: 5
tgctcttgaa cttctcattg tagttagtat gaccgttgcc aggattaatc tctccaatcc       60
actcaaggcc                                                              70

<210> SEQ ID NO 6
<211> LENGTH: 70

```
<212> TYPE: DNA
<213> ORGANISM: Artificial Sequence
<220> FEATURE:
<223> OTHER INFORMATION: HBBK4-3U: BBK4 ScFv combinational primer

<400> SEQUENCE: 6
aatgagaagt tcaagagcar ggyaactmtg actskggaca cctctacaag cacagyatac    60 atgsaactca                                                          70

<210> SEQ ID NO 7
<211> LENGTH: 70
<212> TYPE: DNA
<213> ORGANISM: Artificial Sequence
<220> FEATURE:
<223> OTHER INFORMATION: HBBK4-3D: BBK4 ScFv combinational primer

<400> SEQUENCE: 7
taaaagatct tgcacagtaa tagaccgcgg wgtcctcaga ccgcaggctg ctgagttsca    60 tgtatrctgt                                                          70

<210> SEQ ID NO 8
<211> LENGTH: 70
<212> TYPE: DNA
<213> ORGANISM: Artificial Sequence
<220> FEATURE:
<223> OTHER INFORMATION: HBBK4-4U: BBK4 ScFv combinational primer

<400> SEQUENCE: 8
tactgtgcaa gatcttttac tacggcacgg gcgtttgctt actggggcca agggaccctc    60
gtgaccgtct                                                          70

<210> SEQ ID NO 9
<211> LENGTH: 70
<212> TYPE: DNA
<213> ORGANISM: Artificial Sequence
<220> FEATURE:
<223> OTHER INFORMATION: HBBK4-4D: BBK4 ScFv combinational primer

<400> SEQUENCE: 9
ctgagccgcc gccgcctgag ccgccgccgc ctgagccgcc gccgctgag gagacggtca    60 cgagggtccc                                                          70

<210> SEQ ID NO 10
<211> LENGTH: 70
<212> TYPE: DNA
<213> ORGANISM: Artificial Sequence
<220> FEATURE:
<223> OTHER INFORMATION: HBBK4-5U: BBK4 ScFv combinational primer

<400> SEQUENCE: 10
tcaggcggcg gcggctcaga crttgtgatg actcagtctc cagccttctt atctgtgact    60
ccaggagaga                                                          70

<210> SEQ ID NO 11
<211> LENGTH: 70
<212> TYPE: DNA
<213> ORGANISM: Artificial Sequence
<220> FEATURE:
<223> OTHER INFORMATION: HBBK4-5D: BBK4 ScFv combinational primer

<400> SEQUENCE: 11
agtgtaagta gtcgctaata gtctggctgg ccctgcaagt aakagtcact ttctctcctg    60
```

```
gagtcacaga                                                              70

<210> SEQ ID NO 12
<211> LENGTH: 70
<212> TYPE: DNA
<213> ORGANISM: Artificial Sequence
<220> FEATURE:
<223> OTHER INFORMATION: HBBK4-6U: BBK4 ScFv combinational primer

<400> SEQUENCE: 12
attagcgact acttacactg gtatcaacaa aaacccgatc aakctcccaa acttctcatc       60
aaatatgctt                                                              70

<210> SEQ ID NO 13
<211> LENGTH: 70
<212> TYPE: DNA
<213> ORGANISM: Artificial Sequence
<220> FEATURE:
<223> OTHER INFORMATION: HBBK4-6D: BBK4 ScFv combinational primer

<400> SEQUENCE: 13
tccctgatcc actgccactg aacctggagg gaaycccaga gatggattgg gaagcatatt       60
tgatgagaag                                                              70

<210> SEQ ID NO 14
<211> LENGTH: 70
<212> TYPE: DNA
<213> ORGANISM: Artificial Sequence
<220> FEATURE:
<223> OTHER INFORMATION: HBBK4-7U: BBK4 ScFv combinational primer

<400> SEQUENCE: 14
agtggcagtg gatcagggac tgatttcact yttastatct cgtcgstcga ggcagaagat      60 gytgsgrygt                                                              70

<210> SEQ ID NO 15
<211> LENGTH: 70
<212> TYPE: DNA
<213> ORGANISM: Artificial Sequence
<220> FEATURE:
<223> OTHER INFORMATION: HBBK4-7D: BBK4 ScFv combinational primer

<400> SEQUENCE: 15
tagttccttg accgaaagtt gggggaaagc tgtgaccatc ttgacagtaa tacrycscar       60
catcttctgc                                                              70

<210> SEQ ID NO 16
<211> LENGTH: 57
<212> TYPE: DNA
<213> ORGANISM: Artificial Sequence
<220> FEATURE:
<223> OTHER INFORMATION: HBBK4-8D: BBK4 ScFv combinational primer

<400> SEQUENCE: 16
gagtcattct cgacttgcgg ccgctttgat ctcgagttta gttccttgac cgaaagt         57

<210> SEQ ID NO 17
<211> LENGTH: 20
<212> TYPE: DNA
<213> ORGANISM: Artificial Sequence
<220> FEATURE:
<223> OTHER INFORMATION: HBBK4 SfiI-U: BBK4 ScFv combinational primer

<400> SEQUENCE: 17
```
actgcggccc agccggccat                                          20

<210> SEQ ID NO 18
<211> LENGTH: 20
<212> TYPE: DNA
<213> ORGANISM: Artificial Sequence
<220> FEATURE:
<223> OTHER INFORMATION: HBBK4 NotI-D: BBK4 ScFv combinational primer

<400> SEQUENCE: 18
ttagttcctt gaccgaaagt                                          20

<210> SEQ ID NO 19
<211> LENGTH: 20
<212> TYPE: DNA
<213> ORGANISM: Artificial Sequence
<220> FEATURE:
<223> OTHER INFORMATION: recognition site for resriction enzyme SfiI

<400> SEQUENCE: 19
actgcggccc agccggccat                                          20

<210> SEQ ID NO 20
<211> LENGTH: 20
<212> TYPE: DNA
<213> ORGANISM: Artificial Sequence
<220> FEATURE:
<223> OTHER INFORMATION: recognition site for resriction enzyme NotI

<400> SEQUENCE: 20
ttagttcctt gaccgaaagt                                          20

<210> SEQ ID NO 21
<211> LENGTH: 20
<212> TYPE: DNA
<213> ORGANISM: Artificial Sequence
<220> FEATURE:
<223> OTHER INFORMATION: forward primer (sense) for Annexin4

<400> SEQUENCE: 21
aatcaaccag acataccagc                                          20

<210> SEQ ID NO 22
<211> LENGTH: 20
<212> TYPE: DNA
<213> ORGANISM: Artificial Sequence
<220> FEATURE:
<223> OTHER INFORMATION: reverse primer (anti-sense) for Annexin4

<400> SEQUENCE: 22
tcttcaaagc ttccagatgt                                          20

<210> SEQ ID NO 23
<211> LENGTH: 18
<212> TYPE: DNA
<213> ORGANISM: Artificial Sequence
<220> FEATURE:
<223> OTHER INFORMATION: forward primer (sense) for Klrg1

<400> SEQUENCE: 23
ctttgcaatg gtggcttt                                            18

<210> SEQ ID NO 24
<211> LENGTH: 18
<212> TYPE: DNA

```
<213> ORGANISM: Artificial Sequence
<220> FEATURE:
<223> OTHER INFORMATION: reverse primer (anti-sense) for Klrg1

<400> SEQUENCE: 24
ctccagccat caatgttc                                                   18

<210> SEQ ID NO 25
<211> LENGTH: 20
<212> TYPE: DNA
<213> ORGANISM: Artificial Sequence
<220> FEATURE:
<223> OTHER INFORMATION: forward primer (sense) for CD68 Ag

<400> SEQUENCE: 25
gcatatctgt tttgaatccc                                                 20

<210> SEQ ID NO 26
<211> LENGTH: 20
<212> TYPE: DNA
<213> ORGANISM: Artificial Sequence
<220> FEATURE:
<223> OTHER INFORMATION: reverse primer (anti-sense) for CD68 Ag

<400> SEQUENCE: 26
ccttagagag agcaggtcaa                                                 20

<210> SEQ ID NO 27
<211> LENGTH: 20
<212> TYPE: DNA
<213> ORGANISM: Artificial Sequence
<220> FEATURE:
<223> OTHER INFORMATION: forward primer (sense) for THRI13

<400> SEQUENCE: 27
gtgatgacca ccgtactctt                                                 20

<210> SEQ ID NO 28
<211> LENGTH: 20
<212> TYPE: DNA
<213> ORGANISM: Artificial Sequence
<220> FEATURE:
<223> OTHER INFORMATION: reverse primer (anti-sense) for THRI13

<400> SEQUENCE: 28
gcattgacta ctcggatagc                                                 20

<210> SEQ ID NO 29
<211> LENGTH: 20
<212> TYPE: DNA
<213> ORGANISM: Artificial Sequence
<220> FEATURE:
<223> OTHER INFORMATION: forward primer (sense) for NKG2

<400> SEQUENCE: 29
cgattcaccc ttaacacatt                                                 20

<210> SEQ ID NO 30
<211> LENGTH: 20
<212> TYPE: DNA
<213> ORGANISM: Artificial Sequence
<220> FEATURE:
<223> OTHER INFORMATION: reverse primer (anti-sense) for NKG2

<400> SEQUENCE: 30
gctggaattt tgagacaaac                                                 20
```

<210> SEQ ID NO 31
<211> LENGTH: 20
<212> TYPE: DNA
<213> ORGANISM: Artificial Sequence
<220> FEATURE:
<223> OTHER INFORMATION: forward primer (sense) for TGF-BETA1

<400> SEQUENCE: 31
ttgacgtcac tggagttgta                                         20

<210> SEQ ID NO 32
<211> LENGTH: 20
<212> TYPE: DNA
<213> ORGANISM: Artificial Sequence
<220> FEATURE:
<223> OTHER INFORMATION: reverse primer (anti-sense) for TGF-BETA1

<400> SEQUENCE: 32
aatagttggt atccagggct                                         20

<210> SEQ ID NO 33
<211> LENGTH: 20
<212> TYPE: DNA
<213> ORGANISM: Artificial Sequence
<220> FEATURE:
<223> OTHER INFORMATION: forward primer (sense) for PRP1

<400> SEQUENCE: 33
cagcattacc acaagaatga                                         20

<210> SEQ ID NO 34
<211> LENGTH: 20
<212> TYPE: DNA
<213> ORGANISM: Artificial Sequence
<220> FEATURE:
<223> OTHER INFORMATION: reverse primer (anti-sense) for PRP1

<400> SEQUENCE: 34
cccacattcc agaagattta                                         20

<210> SEQ ID NO 35
<211> LENGTH: 20
<212> TYPE: DNA
<213> ORGANISM: Artificial Sequence
<220> FEATURE:
<223> OTHER INFORMATION: forward primer (sense) for IL-1R II

<400> SEQUENCE: 35
cgatgcaggc tattacagat                                         20

<210> SEQ ID NO 36
<211> LENGTH: 20
<212> TYPE: DNA
<213> ORGANISM: Artificial Sequence
<220> FEATURE:
<223> OTHER INFORMATION: reverse primer (anti-sense) for IL-1R II

<400> SEQUENCE: 36
atcaaaaatc agcgacactt                                         20

<210> SEQ ID NO 37
<211> LENGTH: 18
<212> TYPE: DNA
<213> ORGANISM: Artificial Sequence
<220> FEATURE:

<223> OTHER INFORMATION: forward primer (sense) for Granzyme B

<400> SEQUENCE: 37
cccaggcgca atgctaat                                                 18

<210> SEQ ID NO 38
<211> LENGTH: 18
<212> TYPE: DNA
<213> ORGANISM: Artificial Sequence
<220> FEATURE:
<223> OTHER INFORMATION: reverse primer (anti-sense) for Granzyme B

<400> SEQUENCE: 38
ccaggataag aaactcga                                                 18

<210> SEQ ID NO 39
<211> LENGTH: 18
<212> TYPE: DNA
<213> ORGANISM: Artificial Sequence
<220> FEATURE:
<223> OTHER INFORMATION: forward primer (sense) for GAPDH

<400> SEQUENCE: 39
gaacgggaag cttgtcat                                                 18

<210> SEQ ID NO 40
<211> LENGTH: 18
<212> TYPE: DNA
<213> ORGANISM: Artificial Sequence
<220> FEATURE:
<223> OTHER INFORMATION: reverse primer (anti-sense) for GAPDH

<400> SEQUENCE: 40
ctaagcagtt ggtggtgc                                                 18

<210> SEQ ID NO 41
<211> LENGTH: 20
<212> TYPE: DNA
<213> ORGANISM: Artificial Sequence
<220> FEATURE:
<223> OTHER INFORMATION: forward primer (sense) for TIM-3

<400> SEQUENCE: 41
atccagcaga taccagctaa                                               20

<210> SEQ ID NO 42
<211> LENGTH: 20
<212> TYPE: DNA
<213> ORGANISM: Artificial Sequence
<220> FEATURE:
<223> OTHER INFORMATION: reverse primer (anti-sense) for TIM-3

<400> SEQUENCE: 42
tccattgtta ttatggaggg                                               20

<210> SEQ ID NO 43
<211> LENGTH: 20
<212> TYPE: DNA
<213> ORGANISM: Artificial Sequence
<220> FEATURE:
<223> OTHER INFORMATION: forward primer (sense) for IL-4 IG 1

<400> SEQUENCE: 43
gtatcttcac tttccgggat                                               20

```
<210> SEQ ID NO 44
<211> LENGTH: 19
<212> TYPE: DNA
<213> ORGANISM: Artificial Sequence
<220> FEATURE:
<223> OTHER INFORMATION: reverse primer (anti-sense) for IL-4 IG 1

<400> SEQUENCE: 44
gaggtagaag aagccctcc                                                19

<210> SEQ ID NO 45
<211> LENGTH: 20
<212> TYPE: DNA
<213> ORGANISM: Artificial Sequence
<220> FEATURE:
<223> OTHER INFORMATION: forward primer (sense) for PLECKSTRIN

<400> SEQUENCE: 45
actgaatctg gagaaggaca                                               20

<210> SEQ ID NO 46
<211> LENGTH: 20
<212> TYPE: DNA
<213> ORGANISM: Artificial Sequence
<220> FEATURE:
<223> OTHER INFORMATION: reverse primer (anti-sense) for PLECKSTRIN

<400> SEQUENCE: 46
ttcagtaaac atccctgctt                                               20

<210> SEQ ID NO 47
<211> LENGTH: 20
<212> TYPE: DNA
<213> ORGANISM: Artificial Sequence
<220> FEATURE:
<223> OTHER INFORMATION: forward primer (sense) for TIP2

<400> SEQUENCE: 47
aaagcaaagc aaatgaagag                                               20

<210> SEQ ID NO 48
<211> LENGTH: 20
<212> TYPE: DNA
<213> ORGANISM: Artificial Sequence
<220> FEATURE:
<223> OTHER INFORMATION: reverse primer (anti-sense) for TIP2

<400> SEQUENCE: 48
tcagtggagg aatggtaatc                                               20

<210> SEQ ID NO 49
<211> LENGTH: 20
<212> TYPE: DNA
<213> ORGANISM: Artificial Sequence
<220> FEATURE:
<223> OTHER INFORMATION: forward primer (sense) for LAG3

<400> SEQUENCE: 49
gtctccatca cgtacaacct                                               20

<210> SEQ ID NO 50
<211> LENGTH: 20
<212> TYPE: DNA
<213> ORGANISM: Artificial Sequence
<220> FEATURE:
<223> OTHER INFORMATION: reverse primer (anti-sense) for LAG3
```

<210> SEQ ID NO 51
<211> LENGTH: 20
<212> TYPE: DNA
<213> ORGANISM: Artificial Sequence
<220> FEATURE:
<223> OTHER INFORMATION: forward primer (sense) for KLRG2-A1

<400> SEQUENCE: 51
tcctccagag aaactcattg                                               20

<210> SEQ ID NO 52
<211> LENGTH: 20
<212> TYPE: DNA
<213> ORGANISM: Artificial Sequence
<220> FEATURE:
<223> OTHER INFORMATION: reverse primer (anti-sense) for KLRG2-A1

<400> SEQUENCE: 52
tacagttttt ggaaatgcag                                               20

<210> SEQ ID NO 53
<211> LENGTH: 20
<212> TYPE: DNA
<213> ORGANISM: Artificial Sequence
<220> FEATURE:
<223> OTHER INFORMATION: forward primer (sense) for CD27

<400> SEQUENCE: 53
gctgaatctc acagttcctc                                               20

<210> SEQ ID NO 54
<211> LENGTH: 19
<212> TYPE: DNA
<213> ORGANISM: Artificial Sequence
<220> FEATURE:
<223> OTHER INFORMATION: reverse primer (anti-sense) for CD27

<400> SEQUENCE: 54
ccagtgtcac ctggatatg                                                19

<210> SEQ ID NO 55
<211> LENGTH: 18
<212> TYPE: DNA
<213> ORGANISM: Artificial Sequence
<220> FEATURE:
<223> OTHER INFORMATION: forward primer (sense) for PERFORIN

<400> SEQUENCE: 55
gtcacgtcga agtacttg                                                 18

<210> SEQ ID NO 56
<211> LENGTH: 18
<212> TYPE: DNA
<213> ORGANISM: Artificial Sequence
<220> FEATURE:
<223> OTHER INFORMATION: reverse primer (anti-sense) for PERFORIN

<400> SEQUENCE: 56
atggctgata gcctgtct                                                 18

<210> SEQ ID NO 57
<211> LENGTH: 18

—continued

<400> SEQUENCE: 50
cacaaatctt tcctttccag                                               20

```
<212> TYPE: DNA
<213> ORGANISM: Artificial Sequence
<220> FEATURE:
<223> OTHER INFORMATION: forward primer (sense) for IFN-GAMMA

<400> SEQUENCE: 57
aacgctacac actgcatc                                                  18

<210> SEQ ID NO 58
<211> LENGTH: 18
<212> TYPE: DNA
<213> ORGANISM: Artificial Sequence
<220> FEATURE:
<223> OTHER INFORMATION: reverse primer (anti-sense) for IFN-GAMMA

<400> SEQUENCE: 58
gccgtggcag taacagcc                                                  18

<210> SEQ ID NO 59
<211> LENGTH: 1419
<212> TYPE: DNA
<213> ORGANISM: Homo sapiens
<220> FEATURE:
<223> OTHER INFORMATION: base sequence of HBBK4-75G1

<400> SEQUENCE: 59
```

| | | | |
|---|---|---|---|
| gatctcacca tgggatggag ctgtatcatc ctcttcttgg tagcaacagc tacaggtgtc | 60 |
| cactcccagg tgcagctgca gcagtctggg gctgaagtaa taaagcctgg ggcttcagtg | 120 |
| aagctttcct gcaaggcttc tggctacacc ttcagcagct actggatgca ctgggtgagg | 180 |
| caggcacctg gacaaggcct tgagtggatt ggagagatta tcctggcaac ggtcatact | 240 |
| aactacaatg agaagttcaa gagcagggca actctgactg gggacacctc tacaagcaca | 300 |
| gtatacatgg aactcagcag cctgcggtct gaggacaccg cggtctatta ctgtgcaaga | 360 |
| tcttttacta cggcacgggc gtttgcttac tggggccaag ggaccctcgt gaccgtctcc | 420 |
| tcagcttcca ccaagggccc atcggtcttc cccctggcac cctcctccaa aagcacctct | 480 |
| gggggcacag cggccctggg ctgcctggtc aaggactact ccccgaacc ggtgacggtg | 540 |
| tcgtggaact caggcgccct gaccagcggc gtgcacacct tcccggctgt cctacagtcc | 600 |
| tcaggactct actccctcag cagcgtggtg accgtgccct ccagcagctt gggcacccag | 660 |
| acctacatct gcaacgtgaa tcacaagccc agcaacacca aggtggacaa aaaaagtttg | 720 |
| agtcccaaat cttgtgacaa aactcatact tgcccgccgt gcccggctcc ggaactcctg | 780 |
| ggggaccgt cagtcttcct cttccccca aacccaagg acaccctcat gatctcccgg | 840 |
| acccctgagg tcacatgcgt ggtggtggac gtgagccacg aagaccctga ggtcaagttc | 900 |
| aactggtacg tggacggcgt ggaggtgcat aatgccaaga caaagccgcg ggaggagcag | 960 |
| tacaacagca cgtaccgtgt ggtcagcgtc ctcaccgtcc tgcaccagga ctggctgaat | 1020 |
| ggcaaggagt acaagtgcaa ggtctccaac aaagccctcc cagcccccat cgagaaaacc | 1080 |
| atctccaaag ccaaagggca gccccgagaa ccacaggtgt acaccctgcc cccatcccgg | 1140 |
| gaggagatga ccaagaacca ggtcagcctg acctgcctgg tcaaaggctt ctatcccagc | 1200 |
| gacattgccg tggagtggga gagcaatggg cagccggaga caactacaa gaccacgcct | 1260 |
| cccgtgctgg actccgacgg ctccttcttc ctctatagca agctcaccgt ggacaagagc | 1320 |
| aggtggcagc aggggaacgt cttctcatgc tccgtgatgc atgaggctct gcacaaccac | 1380 |
| tacacgcaga agagcctctc cctgtccccg ggtaaatga | 1419 |

<210> SEQ ID NO 60
<211> LENGTH: 472
<212> TYPE: PRT
<213> ORGANISM: Homo sapiens
<220> FEATURE:
<223> OTHER INFORMATION: amino acid sequence of HBBK4-75G1

<400> SEQUENCE: 60

```
Asp Leu Thr Met Gly Trp Ser Cys Ile Ile Leu Phe Leu Val Ala Thr
1               5                   10                  15

Ala Thr Gly Val His Ser Gln Val Gln Leu Gln Gln Ser Gly Ala Glu
            20                  25                  30

Val Ile Lys Pro Gly Ala Ser Val Lys Leu Ser Cys Lys Ala Ser Gly
        35                  40                  45

Tyr Thr Phe Ser Ser Tyr Trp Met His Trp Val Arg Gln Ala Pro Gly
    50                  55                  60

Gln Gly Leu Glu Trp Ile Gly Glu Ile Asn Pro Gly Asn Gly His Thr
65                  70                  75                  80

Asn Tyr Asn Glu Lys Phe Lys Ser Arg Ala Thr Leu Thr Gly Asp Thr
                85                  90                  95

Ser Thr Ser Thr Val Tyr Met Glu Leu Ser Ser Leu Arg Ser Glu Asp
            100                 105                 110

Thr Ala Val Tyr Tyr Cys Ala Arg Ser Phe Thr Thr Ala Arg Ala Phe
        115                 120                 125

Ala Tyr Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Ser Leu
225                 230                 235                 240

Ser Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365
```

```
Arg Glu Pro Gln Val Tyr Thr Leu Pro Pro Ser Arg Glu Glu Met Thr
    370                 375                 380
Lys Asn Gln Val Ser Leu Thr Cys Leu Val Lys Gly Phe Tyr Pro Ser
385                 390                 395                 400
Asp Ile Ala Val Glu Trp Glu Ser Asn Gly Gln Pro Glu Asn Asn Tyr
                405                 410                 415
Lys Thr Thr Pro Pro Val Leu Asp Ser Asp Gly Ser Phe Phe Leu Tyr
            420                 425                 430
Ser Lys Leu Thr Val Asp Lys Ser Arg Trp Gln Gln Gly Asn Val Phe
        435                 440                 445
Ser Cys Ser Val Met His Glu Ala Leu His Asn His Tyr Thr Gln Lys
    450                 455                 460
Ser Leu Ser Leu Ser Pro Gly Lys
465                 470

<210> SEQ ID NO 61
<211> LENGTH: 1407
<212> TYPE: DNA
<213> ORGANISM: Homo sapiens
<220> FEATURE:
<223> OTHER INFORMATION: base sequence of HBBK4-75G4

<400> SEQUENCE: 61
gatctcacca tgggatggag ctgtatcatc ctcttcttgg tagcaacagc tacaggtgtc      60
cactcccagg tgcagctgca gcagtctggg gctgaagtaa taaagcctgg ggcttcagtg     120
aagctttcct gcaaggcttc tggctacacc ttcagcagct actggatgca ctgggtgagg     180
caggcacctg gacaaggcct tgagtggatt ggagagatta tcctggcaa cggtcatact     240 aactacaatg agaagttcaa gagcagggca actctgactg gggacaccct acaagcaca     300 gtatacatgg aactcagcag cctgcggtct gaggacaccg cggtctatta ctgtgcaaga     360
tcttttacta cggcacgggc gtttgcttac tggggccaag ggaccctcgt gaccgtctcc     420
tcagcttcca ccaagggccc atccgtcttc ccctggcgc cctgctccag gagcacctcc     480
gagagcacag ccgccctggg ctgcctggtc aaggactact tccccgaacc ggtgacggtg     540
tcgtggaact caggcgccct gaccagcggc gtgcacacct tcccggctgt cctacagtcc     600
tcaggactct actccctcag cagcgtggtg accgtgccct ccagcagctt gggcacgaag     660
acctacacct gcaacgtaga tcacaagccc agcaacacca aggtggacaa gagagttgag     720
tccaaatatg gtcccccatg cccatcatgc ccagcacctg agttcctggg gggaccatca     780
gtcttcctgt tccccccaaa acccaaggac actctcatga tctcccggac ccctgaggtc     840
acgtgcgtgg tggtggacgt gagccaggaa gaccccgagg tccagttcaa ctggtacgtg     900
gatggcgtgg aggtgcataa tgccaagaca aagccgcggg aggagcagtt caacagcacg     960
taccgtgtgg tcagcgtcct caccgtcctg caccaggact ggctgaacgg caaggagtac    1020
aagtgcaagg tctccaacaa aggcctcccg tcctccatcg agaaaccat ctccaaagcc    1080 aaagggcagc cccgagagcc acaggtgtac accctgcccc catcccagga ggagatgacc    1140
aagaaccagg tcagcctgac ctgcctggtc aaaggcttct accccagcga catcgccgtg    1200
gagtgggaga gcaatgggca gccggagaac aactacaaga ccacgcctcc cgtgctggac    1260
tccgacggct ccttcttcct ctacagcagg ctaaccgtgg acaagagcag gtggcaggag    1320
gggaatgtct tctcatgctc cgtgatgcat gaggctctgc acaaccacta cacacagaag    1380
agcctctccc tgtctctggg taaatga                                        1407
```

<210> SEQ ID NO 62
<211> LENGTH: 465
<212> TYPE: PRT
<213> ORGANISM: Homo sapiens
<220> FEATURE:
<223> OTHER INFORMATION: amino acid sequence of HBBK4-75G4

<400> SEQUENCE: 62

```
Met Gly Trp Ser Cys Ile Ile Leu Phe Leu Val Ala Thr Ala Thr Gly
 1               5                  10                  15

Val His Ser Gln Val Gln Leu Gln Gln Ser Gly Ala Glu Val Ile Lys
            20                  25                  30

Pro Gly Ala Ser Val Lys Leu Ser Cys Lys Ala Ser Gly Tyr Thr Phe
        35                  40                  45

Ser Ser Tyr Trp Met His Trp Val Arg Gln Ala Pro Gly Gln Gly Leu
    50                  55                  60

Glu Trp Ile Gly Glu Ile Asn Pro Gly Asn Gly His Thr Asn Tyr Asn
65                  70                  75                  80

Glu Lys Phe Lys Ser Arg Ala Thr Leu Thr Gly Asp Thr Ser Thr Ser
                85                  90                  95

Thr Val Tyr Met Glu Leu Ser Ser Leu Arg Ser Glu Asp Thr Ala Val
            100                 105                 110

Tyr Tyr Cys Ala Arg Ser Phe Thr Thr Ala Arg Ala Phe Ala Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Lys Thr Tyr Thr Cys Asn Val Asp
    210                 215                 220

His Lys Pro Ser Asn Thr Lys Val Asp Lys Arg Val Glu Ser Lys Tyr
225                 230                 235                 240

Gly Pro Pro Cys Pro Ser Cys Pro Ala Pro Glu Phe Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser Gln Glu Asp
        275                 280                 285

Pro Glu Val Gln Phe Asn Trp Tyr Val Asp Gly Val Glu Val His Asn
    290                 295                 300

Ala Lys Thr Lys Pro Arg Glu Glu Gln Phe Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Gly Leu Pro Ser Ser Ile Glu Lys
            340                 345                 350

Thr Ile Ser Lys Ala Lys Gly Gln Pro Arg Glu Pro Gln Val Tyr Thr
        355                 360                 365
```

Leu Pro Pro Ser Gln Glu Glu Met Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Arg Leu Thr Val Asp Lys
            420                 425                 430

Ser Arg Trp Gln Glu Gly Asn Val Phe Ser Cys Ser Val Met His Glu
        435                 440                 445

Ala Leu His Asn His Tyr Thr Gln Lys Ser Leu Ser Leu Ser Leu Gly
    450                 455                 460

Lys
465

<210> SEQ ID NO 63
<211> LENGTH: 713
<212> TYPE: DNA
<213> ORGANISM: Homo sapiens
<220> FEATURE:
<223> OTHER INFORMATION: base sequence of HBBK4-75L

<400> SEQUENCE: 63
gcctggacat gatgaggttc tctgctcagt tccttggtct cctgttgctc tgttttcaag     60
gtaccagatg tgacattgtg atgactcagt ctccagcctt cttatctgtg actccaggag    120
agaaagtgac tattacttgc agggccagcc agactattag cgactactta cactggtatc    180
aacaaaaacc cgatcaagct cccaaacttc tcatcaaata tgcttcccaa tccatctctg    240
ggattccctc caggttcagt ggcagtggat cagggactga tttcactttt actatctcgt    300
cgctcgaggc agaagatgct gcgacgtatt actgtcaaga tggtcacagc tttcccccaa    360
ctttcggtca aggaactaaa ctcgagatca aaactgtggc tgcaccatct gtcttcatct    420
tcccgccatc tgatgagcag ttgaaatctg gaactgcctc tgttgtgtgc ctgctgaata    480
acttctatcc cagagaggcc aaagtacagt ggaaggtgga taacgccctc caatcgggta    540
actcccagga gagtgtcaca gagcaggaca gcaaggacag cacctacagc ctcagcagca    600
ccctgacgct gagcaaagca gactacgaga aacacaaagt ctacgcctgc gaagtcaccc    660
atcagggcct gagttcgccc gtcacaaaga gcttcaacag gggagagtgt tag            713

<210> SEQ ID NO 64
<211> LENGTH: 236
<212> TYPE: PRT
<213> ORGANISM: Homo sapiens
<220> FEATURE:
<223> OTHER INFORMATION: amino acid sequence of HBBK4-75L

<400> SEQUENCE: 64

Leu Asp Met Met Arg Phe Ser Ala Gln Phe Leu Gly Leu Leu Leu Leu
1               5                   10                  15

Cys Phe Gln Gly Thr Arg Cys Asp Ile Val Met Thr Gln Ser Pro Ala
            20                  25                  30

Phe Leu Ser Val Thr Pro Gly Glu Lys Val Thr Ile Thr Cys Arg Ala
        35                  40                  45

Ser Gln Thr Ile Ser Asp Tyr Leu His Trp Tyr Gln Gln Lys Pro Asp
    50                  55                  60

Gln Ala Pro Lys Leu Leu Ile Lys Tyr Ala Ser Gln Ser Ile Ser Gly
65                  70                  75                  80

```
Ile Pro Ser Arg Phe Ser Gly Ser Gly Ser Gly Thr Asp Phe Thr Phe
                85                  90                  95

Thr Ile Ser Ser Leu Glu Ala Glu Asp Ala Ala Thr Tyr Tyr Cys Gln
                100                 105                 110

Asp Gly His Ser Phe Pro Pro Thr Phe Gly Gln Gly Thr Lys Leu Glu
                115                 120                 125

Ile Lys Thr Val Ala Ala Pro Ser Val Phe Ile Phe Pro Pro Ser Asp
        130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
                180                 185                 190

Ser Thr Tyr Ser Leu Ser Ser Thr Leu Thr Leu Ser Lys Ala Asp Tyr
                195                 200                 205

Glu Lys His Lys Val Tyr Ala Cys Glu Val Thr His Gln Gly Leu Ser
        210                 215                 220

Ser Pro Val Thr Lys Ser Phe Asn Arg Gly Glu Cys
225                 230                 235

<210> SEQ ID NO 65
<211> LENGTH: 70
<212> TYPE: PRT
<213> ORGANISM: Homo sapiens
<220> FEATURE:
<223> OTHER INFORMATION: amino acid sequence of BBK-4-H m4B4-H

<400> SEQUENCE: 65

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Ser Ser Tyr
                20                  25                  30

Trp Met His Trp Val Lys Gln Arg Pro Gly Gln Val Leu Glu Trp Ile
            35                  40                  45

Gly Glu Ile Asn Pro Gly Asn Gly His Thr Asn Tyr Asn Glu Lys Phe
        50                  55                  60

Lys Ser Lys Ala Thr Leu
65                  70

<210> SEQ ID NO 66
<211> LENGTH: 70
<212> TYPE: PRT
<213> ORGANISM: Homo sapiens
<220> FEATURE:
<223> OTHER INFORMATION: amino acid sequence of BBK-4-H Human VH1-46/J4

<400> SEQUENCE: 66

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met
```

-continued

```
<210> SEQ ID NO 67
<211> LENGTH: 70
<212> TYPE: PRT
<213> ORGANISM: Homo sapiens
<220> FEATURE:
<223> OTHER INFORMATION: amino acid sequence of BBK-4-H M4B4-H
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: misc_feature
<222> LOCATION: (40)..(40)
<223> OTHER INFORMATION: Xaa can be any naturally occurring amino acid
<220> FEATURE:
<221> NAME/KEY: misc_feature
<222> LOCATION: (67)..(68)
<223> OTHER INFORMATION: Xaa can be any naturally occurring amino acid

<400> SEQUENCE: 67

Gln Val Xaa Leu Xaa Xaa Ser Gly Ala Glu Val Lys Lys Pro Gly Ala
1               5                   10                  15

Ser Val Lys Xaa Ser Cys Lys Ala Ser Gly Tyr Thr Phe Ser Ser Tyr
                20                  25                  30

Trp Met His Trp Val Xaa Gln Xaa Pro Gly Gln Gly Leu Glu Trp Ile
            35                  40                  45

Gly Glu Ile Asn Pro Gly Asn Gly His Thr Asn Tyr Asn Glu Lys Phe
        50                  55                  60

Lys Ser Xaa Xaa Thr Met
65                  70

<210> SEQ ID NO 68
<211> LENGTH: 70
<212> TYPE: PRT
<213> ORGANISM: Homo sapiens
<220> FEATURE:
<223> OTHER INFORMATION: amino acid sequence of BBK-4-H H4B4-H-2
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: misc_feature
<222> LOCATION: (67)..(68)
<223> OTHER INFORMATION: Xaa can be any naturally occurring amino acid
<220> FEATURE:
<221> NAME/KEY: misc_feature
<222> LOCATION: (70)..(70)
<223> OTHER INFORMATION: Xaa can be any naturally occurring amino acid
```

<400> SEQUENCE: 68

Gln Val Gln Leu Gln Gln Ser Gly Ala Glu Val Xaa Lys Pro Gly Ala
1               5                   10                  15

Ser Val Lys Xaa Ser Cys Lys Ala Ser Gly Tyr Thr Phe Ser Ser Tyr
            20                  25                  30

Trp Met His Trp Val Xaa Gln Ala Pro Gly Gln Gly Leu Glu Trp Ile
        35                  40                  45

Gly Glu Ile Asn Pro Gly Asn Gly His Thr Asn Tyr Asn Glu Lys Phe
    50                  55                  60

Lys Ser Xaa Xaa Thr Xaa
65                  70

<210> SEQ ID NO 69
<211> LENGTH: 49
<212> TYPE: PRT
<213> ORGANISM: Homo sapiens
<220> FEATURE:
<223> OTHER INFORMATION: amino acid sequence of BBK-4-H m4B4-H

<400> SEQUENCE: 69

Thr Val Asp Lys Ser Ser Ser Thr Ala Tyr Met Gln Leu Ser Ser Leu
1               5                   10                  15

Thr Ser Glu Asp Ser Ala Val Tyr Tyr Cys Ala Arg Ser Phe Thr Thr
            20                  25                  30

Ala Arg Ala Phe Ala Tyr Trp Gly Gln Gly Thr Leu Val Thr Val Ser
        35                  40                  45

Ser

<210> SEQ ID NO 70
<211> LENGTH: 49
<212> TYPE: PRT
<213> ORGANISM: Homo sapiens
<220> FEATURE:
<223> OTHER INFORMATION: amino acid sequence of BBK-4-H Human VH1-46/J4
<220> FEATURE:
<221> NAME/KEY: misc_feature
<222> LOCATION: (29)..(34)
<223> OTHER INFORMATION: Xaa can be any naturally occurring amino acid

<400> SEQUENCE: 70

Thr Arg Asp Thr Ser Thr Ser Thr Val Tyr Met Glu Leu Ser Ser Leu
1               5                   10                  15

Arg Ser Glu Asp Thr Ala Val Tyr Tyr Cys Ala Arg Xaa Xaa Xaa Xaa
            20                  25                  30

Xaa Xaa Tyr Phe Asp Tyr Trp Gly Gln Gly Thr Leu Val Thr Val Ser
        35                  40                  45

Ser

<210> SEQ ID NO 71
<211> LENGTH: 49
<212> TYPE: PRT
<213> ORGANISM: Homo sapiens
<220> FEATURE:
<223> OTHER INFORMATION: amino acid sequence of BBK-4-H M4B4-H
<220> FEATURE:
<221> NAME/KEY: misc_feature
<222> LOCATION: (21)..(21)
<223> OTHER INFORMATION: Xaa can be any naturally occurring amino acid

<400> SEQUENCE: 71

Thr Arg Asp Thr Ser Thr Ser Thr Val Tyr Met Glu Leu Ser Ser Leu
1               5                   10                  15

```
Arg Ser Glu Asp Xaa Ala Val Tyr Tyr Cys Ala Arg Ser Phe Thr Thr
        20                  25                  30

Ala Arg Ala Phe Ala Tyr Trp Gly Gln Gly Thr Leu Val Thr Val Ser
        35                  40                  45

Ser

<210> SEQ ID NO 72
<211> LENGTH: 49
<212> TYPE: PRT
<213> ORGANISM: Homo sapiens
<220> FEATURE:
<223> OTHER INFORMATION: amino acid sequence of BBK-4-H H4B4-H-2
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid

<400> SEQUENCE: 72

Thr Xaa Asp Thr Ser Thr Ser Thr Xaa Tyr Met Xaa Leu Ser Ser Leu
1               5                   10                  15

Arg Ser Glu Asp Xaa Ala Val Tyr Tyr Cys Ala Arg Ser Phe Thr Thr
        20                  25                  30

Ala Arg Ala Phe Ala Tyr Trp Gly Gln Gly Thr Leu Val Thr Val Ser
        35                  40                  45

Ser

<210> SEQ ID NO 73
<211> LENGTH: 74
<212> TYPE: PRT
<213> ORGANISM: Homo sapiens
<220> FEATURE:
<223> OTHER INFORMATION: amino acid sequence of BBK-4-L m4B4-L

<400> SEQUENCE: 73

Asp Ile Val Met Thr Gln Ser Gln Ala Thr Gln Ser Val Thr Pro Gly
1               5                   10                  15

Asp Arg Val Ser Leu Ser Cys Arg Ala Ser Gln Thr Ile Ser Asp Tyr
        20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
        50                  55                  60

Ser Gly Ser Gly Ser Asp Phe Thr Leu Ser
65                  70

<210> SEQ ID NO 74
<211> LENGTH: 74
<212> TYPE: PRT
<213> ORGANISM: Homo sapiens
<220> FEATURE:
<223> OTHER INFORMATION: amino acid sequence of BBK-4-L Human A14/J2
```

<400> SEQUENCE: 74

Asp Val Val Met Thr Gln Ser Pro Ala Phe Leu Ser Val Thr Pro Gly
1               5                   10                  15

Glu Lys Val Thr Ile Thr Cys Gln Ala Ser Glu Gly Ile Gly Asn Tyr
            20                  25                  30

Leu Tyr Trp Tyr Gln Gln Lys Pro Asp Gln Ala Pro Lys Leu Leu Ile
        35                  40                  45

Lys Tyr Ala Ser Gln Ser Ile Ser Gly Val Pro Ser Arg Phe Ser Gly
50                  55                  60

Ser Gly Ser Gly Thr Asp Phe Thr Phe Thr
65                  70

<210> SEQ ID NO 75
<211> LENGTH: 74
<212> TYPE: PRT
<213> ORGANISM: Homo sapiens
<220> FEATURE:
<223> OTHER INFORMATION: amino acid sequence of BBK-4-L H4B4-L
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (21)..(22)
<223> OTHER INFORMATION: Xaa can be any naturally occurring amino acid
<220> FEATURE:
<221> NAME/KEY: misc_feature
<222> LOCATION: (40)..(40)
<223> OTHER INFORMATION: Xaa can be any naturally occurring amino acid
<220> FEATURE:
<221> NAME/KEY: misc_feature
<222> LOCATION: (42)..(43)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (58)..(58)
<223> OTHER INFORMATION: Xaa can be any naturally occurring amino acid
<220> FEATURE:
<221> NAME/KEY: misc_feature
<222> LOCATION: (69)..(69)
<223> OTHER INFORMATION: Xaa can be any naturally occurring amino acid

<400> SEQUENCE: 75

Asp Xaa Xaa Met Thr Gln Ser Pro Ala Xaa Leu Ser Val Thr Pro Gly
1               5                   10                  15

Glu Lys Val Thr Xaa Xaa Cys Arg Ala Ser Gln Thr Ile Ser Asp Tyr
            20                  25                  30

Leu His Trp Tyr Gln Gln Lys Xaa Asp Xaa Xaa Pro Xaa Leu Leu Ile
        35                  40                  45

Lys Tyr Ala Ser Gln Ser Ile Ser Gly Xaa Pro Ser Arg Phe Ser Gly
50                  55                  60

Ser Gly Ser Gly Xaa Asp Phe Thr Phe Thr
65                  70

<210> SEQ ID NO 76
<211> LENGTH: 74
<212> TYPE: PRT
<213> ORGANISM: Homo sapiens

```
<220> FEATURE:
<223> OTHER INFORMATION: amino acid sequence of BBK-4-L H4B4-L-2
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (43)..(43)
<223> OTHER INFORMATION: Xaa can be any naturally occurring amino acid
<220> FEATURE:
<221> NAME/KEY: misc_feature
<222> LOCATION: (58)..(58)
<223> OTHER INFORMATION: Xaa can be any naturally occurring amino acid
<220> FEATURE:
<221> NAME/KEY: misc_feature
<222> LOCATION: (73)..(74)
<223> OTHER INFORMATION: Xaa can be any naturally occurring amino acid

<400> SEQUENCE: 76

Asp Xaa Val Met Thr Gln Ser Pro Ala Phe Leu Ser Val Thr Pro Gly
1               5                   10                  15

Glu Lys Val Thr Xaa Thr Cys Arg Ala Ser Gln Thr Ile Ser Asp Tyr
                20                  25                  30

Leu His Trp Tyr Gln Gln Lys Pro Asp Gln Xaa Pro Lys Leu Leu Ile
            35                  40                  45

Lys Tyr Ala Ser Gln Ser Ile Ser Gly Xaa Pro Ser Arg Phe Ser Gly
    50                  55                  60

Ser Gly Ser Gly Thr Asp Phe Thr Xaa Xaa
65                  70

<210> SEQ ID NO 77
<211> LENGTH: 33
<212> TYPE: PRT
<213> ORGANISM: Homo sapiens
<220> FEATURE:
<223> OTHER INFORMATION: amino acid sequence of BBK-4-L m4B4-L

<400> SEQUENCE: 77

Ile Asn Ser Val Glu Pro Glu Asp Val Gly Val Tyr Tyr Cys Gln Asp
1               5                   10                  15

Gly His Ser Phe Pro Pro Thr Phe Gly Gly Gly Thr Lys Leu Glu Ile
                20                  25                  30

Lys

<210> SEQ ID NO 78
<211> LENGTH: 33
<212> TYPE: PRT
<213> ORGANISM: Homo sapiens
<220> FEATURE:
<223> OTHER INFORMATION: amino acid sequence of BBK-4-L Human A14/J2

<400> SEQUENCE: 78

Ile Ser Ser Leu Glu Ala Glu Asp Ala Ala Thr Tyr Tyr Cys Gln Gln
1               5                   10                  15

Gly Asn Lys His Pro Trp Thr Phe Gly Gln Gly Thr Lys Leu Glu Ile
                20                  25                  30

Lys

<210> SEQ ID NO 79
<211> LENGTH: 33
```

```
<212> TYPE: PRT
<213> ORGANISM: Homo sapiens
<220> FEATURE:
<223> OTHER INFORMATION: amino acid sequence of BBK-4-L H4B4-L
<220> FEATURE:
<221> NAME/KEY: misc_feature
<222> LOCATION: (26)..(26)
<223> OTHER INFORMATION: Xaa can be any naturally occurring amino acid

<400> SEQUENCE: 79

Ile Ser Ser Leu Glu Ala Glu Asp Ala Ala Thr Tyr Tyr Cys Gln Asp
1               5                   10                  15

Gly His Ser Phe Pro Pro Thr Phe Gly Xaa Gly Thr Lys Leu Glu Ile
            20                  25                  30

Lys

<210> SEQ ID NO 80
<211> LENGTH: 33
<212> TYPE: PRT
<213> ORGANISM: Homo sapiens
<220> FEATURE:
<223> OTHER INFORMATION: amino acid sequence of BBK-4-L H4B4-L-2
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(11)
<223> OTHER INFORMATION: Xaa can be any naturally occurring amino acid

<400> SEQUENCE: 80

Ile Ser Ser Xaa Glu Ala Glu Asp Xaa Xaa Xaa Tyr Tyr Cys Gln Asp
1               5                   10                  15

Gly His Ser Phe Pro Pro Thr Phe Gly Gln Gly Thr Lys Leu Glu Ile
            20                  25                  30

Lys
```